(12) United States Patent
Xia et al.

(10) Patent No.: US 10,287,225 B2
(45) Date of Patent: May 14, 2019

(54) CHAIN MULTIYNE COMPOUND, PREPARATION METHOD AND APPLICATION THEREOF

(71) Applicant: Xiamen University, Xiamen (CN)

(72) Inventors: Haiping Xia, Xiamen (CN); Qingde Zhuo, Xiamen (CN); Jianfeng Lin, Xiamen (CN); Xiaoxi Zhou, Xiamen (CN); Zhixin Chen, Xiamen (CN); Yifan Shao, Xiamen (CN); Hong Zhang, Xiamen (CN); Xumin He, Xiamen (CN)

(73) Assignee: Xiamen University, Xiamen (CN)

( * ) Notice: Subject to any disclaimer, the term of this patent is extended or adjusted under 35 U.S.C. 154(b) by 0 days.

(21) Appl. No.: 15/811,277

(22) Filed: Nov. 13, 2017

(65) Prior Publication Data

US 2018/0065908 A1 Mar. 8, 2018

Related U.S. Application Data

(63) Continuation of application No. PCT/CN2016/081392, filed on May 9, 2016.

(30) Foreign Application Priority Data

May 13, 2015 (CN) .......................... 2015 1 0241958
Sep. 22, 2015 (CN) .......................... 2015 1 0606889

(51) Int. Cl.

| | |
|---|---|
| *C07C 33/04* | (2006.01) |
| *C07C 41/18* | (2006.01) |
| *C07C 63/00* | (2006.01) |
| *C07C 69/00* | (2006.01) |
| *C07C 205/00* | (2006.01) |
| *C07D 333/24* | (2006.01) |
| *C07C 67/317* | (2006.01) |
| *C07C 69/732* | (2006.01) |
| *C07C 43/178* | (2006.01) |
| *C07C 29/00* | (2006.01) |
| *C07C 303/40* | (2006.01) |
| *C07C 205/56* | (2006.01) |
| *C07F 13/00* | (2006.01) |
| *C07F 15/00* | (2006.01) |
| *C07C 311/17* | (2006.01) |
| *C07C 253/30* | (2006.01) |
| *C07C 255/15* | (2006.01) |
| *H01L 31/00* | (2006.01) |

(Continued)

(52) U.S. Cl.
CPC .............. *C07C 33/04* (2013.01); *C07C 29/00* (2013.01); *C07C 41/18* (2013.01); *C07C 43/178* (2013.01); *C07C 43/1781* (2013.01); *C07C 43/1787* (2013.01); *C07C 67/317* (2013.01); *C07C 69/732* (2013.01); *C07C 205/56* (2013.01); *C07C 253/30* (2013.01); *C07C 255/15* (2013.01); *C07C 303/40* (2013.01); *C07C 311/17* (2013.01); *C07D 333/24* (2013.01); *C07F 13/00* (2013.01); *C07F 15/0033* (2013.01); *C07F 15/0046* (2013.01); *C07F 15/0073* (2013.01); *H01L 31/00* (2013.01); *C07C 69/606* (2013.01); *C07C 205/04* (2013.01); *C07C 2601/02* (2017.05); *C07C 2601/08* (2017.05); *C07C 2601/14* (2017.05); *C07C 2603/50* (2017.05); *C07D 307/40* (2013.01); *C07D 333/16* (2013.01)

(58) Field of Classification Search
CPC ....... C07C 33/04; C07C 41/18; C07C 63/178; C07C 67/317; C07C 69/732; C07C 205/56; C07C 255/15; C07D 333/24
See application file for complete search history.

(56) References Cited

PUBLICATIONS

Kim et al. Cytotoxic Polyacetylenes from the Marine Spong Petrosia sp. Journal of Natural Products, vol. 62, 554-259. (Year: 1999).*

(Continued)

*Primary Examiner* — Sikarl A Witherspoon
(74) *Attorney, Agent, or Firm* — Wayne & Ken, LLC; Tony Hom

(57) ABSTRACT

The present invention relates to fields of organic chemistry and organometallic chemistry. The present invention discloses a chain multiyne compound, a preparation method thereof and an application in synthesizing a fused-ring metallacyclic compound. A structure of the chain multiyne compound in the present invention is shown as Formula I below. The present invention also provides a preparation method of the chain multiyne compound and an application thereof in a synthesis of a fused-ring metallacyclic compound. The chain multiyne compound disclosed in the present invention has multiple functional groups and the structure of the chain multiyne compound is adjustable. The chain multiyne compound can also be used to synthesize the fused-ring metallacyclic compound efficiently. The preparation method of the chain multiyne compound disclosed in the present invention is simple, which can be used to prepare the chain multiyne compound rapidly and efficiently.

Formula I

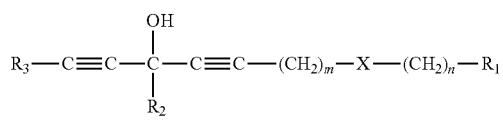

5 Claims, No Drawings

(51) Int. Cl.
    *C07C 69/606*    (2006.01)
    *C07C 205/04*    (2006.01)
    *C07D 307/40*    (2006.01)
    *C07D 333/16*    (2006.01)

(56) References Cited

PUBLICATIONS

Platinum Group Organometallics Based on "Pincer" Complexes: Sensors, Switches, and Catalysts** (Angew Chem Int Ed 2001, 40, 3750 -3781).
Stabilizing Two Classical Antiaromatic Frameworks: Demonstration of Photoacoustic Imaging and the Photothermal Effect in Metalla-aromatics** (Angew Chem Int Ed 2015, 54, 6181 -6185).
Cyclometalated Phosphine-Based Pincer Complexes: Mechanistic Insight in Catalysis, Coordination, and Bond Activation (Chem Rev 2003, 103, 1759-1792).
NCN—pincer palladium complexes with multiple anchoring points for functional groups (Coord Chem Rev 2004, 248, 2275-2282).
Metal complexes with 'pincer'-type ligands incorporating N-heterocyclic carbene functionalities (Coord Chem Rev 2007, 251, 610-641).
Transition Metal-Carbon Bonds. Part XLII. Complexes of Nickel, Palladium, Platinum, Rhodium and Iridium with the Tridentate Ligand 2,6-Bis[(di-t-butylphosphino)methyl]phenyl t (J Chem Soc Dalton Trans 1976, 1020-1024).
Synthesis of Some Bioactive Acetylenic Alcohols, Components of the Marine Sponge Cribrochalina vasculum (J Org Chem 1993,58, 5964-5966).
Stabilization of anti-aromatic and strained five-membered rings with a transition metal (Nat Chem 2013, 5, 698-703).
Planar Mobius aromatic pentalenes incorporating 16 and 18 valence electron osmiums (Nature Communications 53265)—(2014).
New Fragrance System Building by Carbon Dragon and Transition Metal (Haiping Xia)—(2014).
Synthesis of Metal Bridged Fused Ring Aromatic Compounds (Congqing Zhu et al.)—(2012).

\* cited by examiner

CHAIN MULTIYNE COMPOUND, PREPARATION METHOD AND APPLICATION THEREOF

TECHNICAL FIELD

The present disclosure relates to fields of organic chemistry and organometallic chemistry, and more specifically, to a chain multiyne compound, a preparation method thereof and an application in preparing a fused-ring metallacyclic compound.

BACKGROUND

Pincer ligands are tridentate ligands that bind tightly to three adjacent coplanar sites of a metal center in a meridional fashion, which can be divided into different type according to the coordinate atoms, such as NCN-, PCP-type pincer ligands. The concept was first proposed in the 1970s. The corresponding metal complexes containing pincer ligands are named as pincer complexes. Pincer complexes are widely used in the field of coordination chemistry, organic synthesis, homogeneous catalysis and material chemistry due to their properties of excellent stability, reactivity and stereoselectivity (Angew. Chem. Int. Ed. 2001, 40, 3750-3781). In recent years, pincer complexes not only play an important role in fields of CC coupling reaction, inert chemical activation, but also have important applications in the field of solar cells, for example, the terpyridine ruthenium complex (black dye) being widely used as optoelectronic materials.

The structure, reactivity, as well as applications studies of pincer complexes have achieved significant progress since the pincer complex first reported in 1976 (J. Chem. Soc. Dalton Trans 1976, 1020-1024). At present, most of the reported pincer complexes contain pincer ligands of NCN- (Coord. Chem. Rev., 2007, 251, 610-641; Coord. Chem. Rev., 2004, 248, 2275-2282), NNN-, PCP type (Chem. Rev., 2003, 103, 1759-1792), PCO- or SCS-type, in which there is at least one hetero coordination atoms. Pincer complexes with carbon exclusively as the bonding atoms (i.e., CCC-type pincer complexes) are rare. In 2013, Xia et al. reported novel fused-ring metallacyclic compounds, metallapentalynes, which can be regarded as a new kind of CCC-type pincer complexes (Nat. Chem. 2013, 5, 698-703). These CCC-type pincer complexes exhibit unique properties, such as aggregation induced emission enhancement, large Stokes shifts and long lifetime, broad absorption from the ultraviolet-visible to the near-infrared region and excellent photoacoustic and photothermal properties, thus possess potential applications in biomedicine and solar energy utilization Although CCC-type pincer complexes have a good application prospect, how to synthesize these complexes efficiently remains a big challenge due to lack of appropriate CCC pincer ligand or ligand precursor. Therefore, a development and synthesis of the CCC-type pincer ligand or CCC-type pincer ligand precursor are particularly important.

SUMMARY

In order to solve a problem of direct synthesizing a fused-ring metallacyclic compound from a pincer ligand, the present invention proposes a chain multiyne compound, a preparation method thereof and the application thereof in synthesizing a fused-ring metallacyclic compound. The chain multiyne compound provided by the invention has multiple functional groups. The preparation method of the chain multiyne compound is simple; a structure of the chain multiyne compound is adjustable, and can be directly used to synthesize the metallacyclic compound.

Applicants of the present invention have found that the chain multiyne compound can be used to synthesize a fused-ring metallacyclic compound directly as CCC-type pincer ligand by quantities of research. Furthermore, the inventors have found that a chain multiyne compound can be obtained by performing a metal exchange reaction of a terminal alkyne with an organometallic reagent in an aprotic solvent and further contacting and reacting the obtained reaction mixture with alkynylaldehyde or alkynylketone. The chain multiyne compound can directly react with a metal complex to obtain the fused-ring metallacyclic compound. Thus, the present invention has been completed.

According to the first aspect of the present invention, this invention discloses a chain multiyne compound, wherein the chain multiyne compound has a structure of Formula I shown below:

Formula I

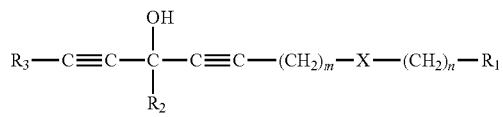

wherein X is any one of —O—, —S—, —$CR_4R_5$—, —$SiR_6R_7$— and —$NR_8$—; the $R_4$, $R_5$, $R_6$, $R_7$, $R_8$ are any one of hydrogen, $C_1$-$C_{20}$ alkyl, $C_1$-$C_{20}$ ester, $C_1$-$C_{20}$ acyl, $C_3$-$C_{20}$ cycloalkyl, $C_1$-$C_{20}$ alkyl halide, nitrile group, nitryl, substituted or unsubstituted aryl and

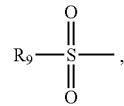

respectively and independently.

The $R_9$ is any one of $C_1$-$C_8$ alkyl and substituted or unsubstituted phenyl.

$R_1$ is any one of nitrile group, substituted or unsubstituted $C_2$-$C_{30}$ alkynyl, substituted or unsubstituted $C_4$-$C_{30}$ multiyne, substituted or unsubstituted $C_3$-$C_{30}$ cumulene, and $R_1$ does not contain a structure unit of —C≡CCH(OH)C≡C—.

$R_2$ and $R_3$ are any one of hydrogen, substituted or unsubstituted aryl, substituted or unsubstituted $C_1$-$C_8$ alkyl, substituted or unsubstituted $C_1$-$C_8$ alkoxy, substituted or unsubstituted $C_1$-$C_8$ alkyithiol, substituted or unsubstituted $C_3$-$C_8$ cycloalkyl and substituted or unsubstituted $C_2$-$C_8$ alkynyl, respectively and independently. $R_2$ and $R_3$ do not contain a structure unit of —C≡CCH(OH)C≡C—.

m and n are integers from 1-6, respectively, and m+n<8.

According to the second aspect of the present invention, this invention discloses a preparation method of the chain multiyne compound, comprising:

step a: performing a metal exchange reaction of a compound of Formula II with an organometallic reagent $RM_1$ and/or $RM_2Z$ in an aprotic solvent, and obtaining a reaction mixture;

step b: contacting and reacting the obtained reaction mixture with a compound of Formula III, obtaining a reaction mixture containing a chain multiyne compound with a protection group Y of Formula IV;

step c: taking off the protection group Y from the chain multiyne compound with a protection group Y of Formula IV of the obtained reaction mixture in step b, and obtaining the chain multiyne compound of Formula I:

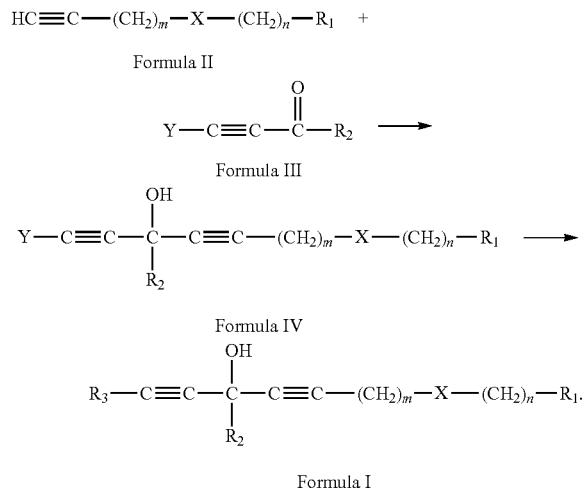

Wherein, Y is any one of trimethylsilyl (TMS), triethylsilyl (TES) and triisopropylsilyl (TIPS).

R of the organometallic reagent $RM_1$ and/or $RM_2Z$ is any one of $C_1$-$C_8$ alkyl, phenyl and —$NR_{10}R_{11}$. The $R_{10}$ and $R_{11}$ are any one of hydrogen, $C_1$-$C_8$ alkyl and trimethylsilyl, respectively and independently. $M_1$ is lithium, or sodium or potassium. $M_2$ is magnesium. Z is chlorine, or bromine or iodine.

Or, step a: performing a metal exchange reaction of a compound of Formula II with an organometallic reagent $RM_1$ and/or $RM_2Z$ in an aprotic solvent, and obtaining a reaction mixture containing;

step b: reacting the obtained reaction mixture with a compound of Formula V, obtaining a mixture containing the chain multiyne compound of Formula I.

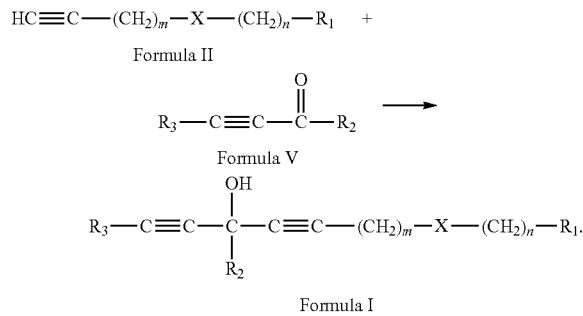

Wherein R of the organometallic reagent $RM_1$ and/or $RM_2Z$ is any one of $C_1$-$C_8$ alkyl, phenyl and —$NR_{10}R_{11}$. The $R_{10}$ and $R_{11}$ are any one of hydrogen, $C_1$-$C_8$ alkyl and trimethylsilyl, respectively and independently. $M_1$ of the organometallic reagent $RM_1$ is lithium, or sodium or potassium. $M_2$ of the $RM_2Z$ is magnesium. Z of the $RM_2Z$ is chlorine, or bromine or iodine.

According to the third aspect of the present invention, this invention discloses an application of the chain multiyne compound in synthesizing a fused-ring metallacyclic compound.

The chain multiyne compound disclosed in the present invention has multiple functional groups and the structure of the chain multiyne compound is adjustable and the chain multiyne compound can also be used to synthesize a fused-ring metallacyclic compound efficiently. The preparation method disclosed in the present invention of the chain multiyne compound is simple, which is able to prepare the chain multiyne compound rapidly and efficiently.

Other characteristics and advantages of the present invention are described in details by following detailed embodiments.

DETAILED DESCRIPTION

Detailed description of the present invention is given below. It should be understood that, the specific embodiments described herein are only used to describe and explain the present invention, and are not intended to limit the present invention.

According to the first aspect of the present invention, this invention discloses a chain multiyne compound, wherein the chain multiyne compound has a structure of Formula I shown below:

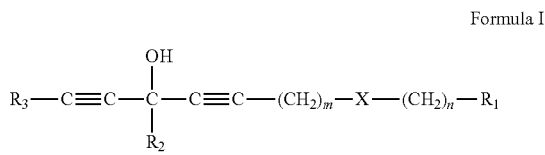

Formula I wherein X is any one of —O—, —S—, —$CR_4R_5$—, —$SiR_6R_7$— and —$NR_8$—; the $R_4$, $R_5$, $R_6$, $R_7$, $R_8$ are any one of hydrogen, $C_1$-$C_{20}$ alkyl, $C_1$-$C_{20}$ ester group, $C_1$-$C_{20}$ acyl, $C_3$-$C_{20}$ cycloalkyl, $C_1$-$C_{20}$ alkyl halide, nitrile group, nitryl, substituted or unsubstituted aryl and

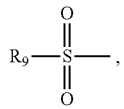

respectively and independently.

The $R_9$ is any one of $C_1$-$C_8$ alkyl and substituted or unsubstituted phenyl.

The $C_1$-$C_8$ alkyl is any one of methyl, ethyl, n-propyl, isopropyl, n-butyl, isobutyl, sec-butyl, tert-butyl, n-pentyl, isopentyl, neopentyl, sec-pentyl, tert-pentyl, n-hexyl, isohexyl, neo-hexyl, sec-hexyl, tert-hexyl, n-heptyl, isoheptyl, neo-heptyl, sec-heptyl, tert-heptyl, n-octyl, isooctyl, neo-octyl, sec-octyl, tert-octyl.

When the R9 is substituted phenyl, a substituent group of the substituted phenyl can be a halogen or a $C_1$-$C_8$ alkyl. The halogen is any one of F, Cl, Br, and I. The $C_1$-$C_8$ alkyl is the same as just mentioned above.

Wherein, the $C_1$-$C_{20}$ alkyl is any one of methyl, ethyl, n-propyl, isopropyl, n-butyl, isobutyl, sec-butyl, tert-butyl, n-pentyl, isopentyl, neopentyl, sec-pentyl, tert-pentyl, n-hexyl, isohexyl, neo-hexyl, sec-hexyl, tert-hexyl, n-heptyl, isoheptyl, neo-heptyl, sec-heptyl, tert-heptyl, n-octyl, isooctyl, neo-octyl, sec-octyl, tert-octyl, n-dodecyl, n-cetyl, n-octadecyl, n-eicosyl,

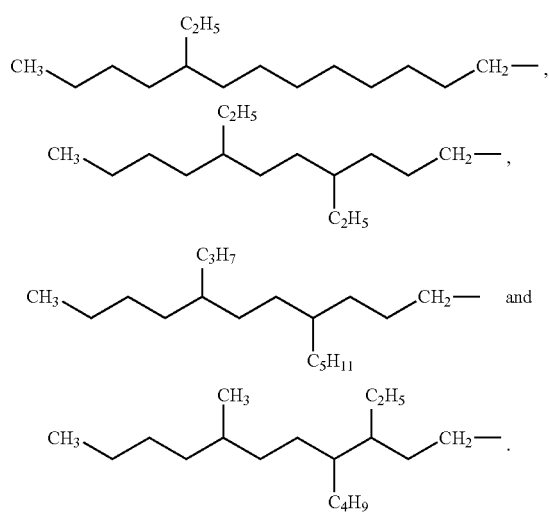

The $C_1$-$C_{20}$ ester refers to a group which has a total carbon atom number of 1-20 and an ester

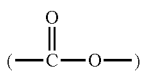

group, and with one hydrogen absent. For example, the $C_1$-$C_{20}$ ester can be any one of

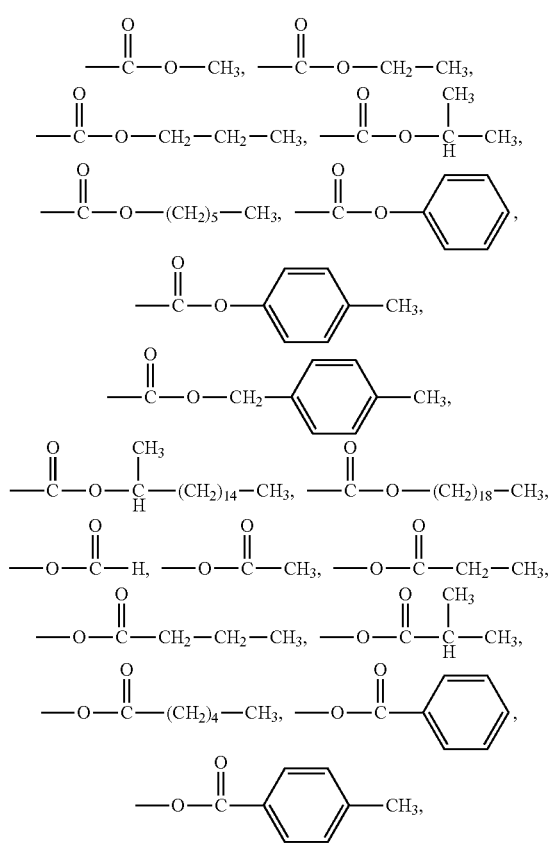

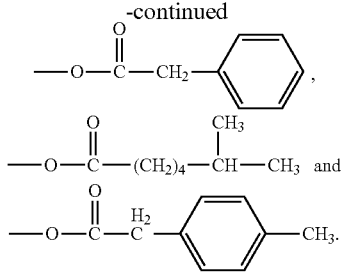

The $C_1$-$C_{20}$ acyl is any one of

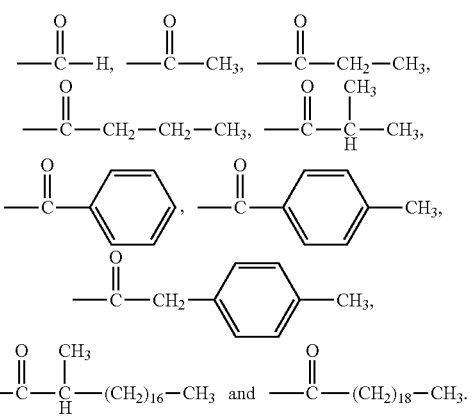

The $C_3$-$C_{20}$ cycloalkyl is any one of cyclopropyl, cyclobutyl, cyclopentyl, cyclohexyl, cycloheptyl, cyclooctyl, cyclodedecyl, cyclooctadecyl, cycloeicosyl.

The $C_1$-$C_{20}$ alkyl halide is a substituted $C_1$-$C_{20}$ alkyl in which at least one hydrogen atom is substituted by at least any one of F, Cl, Br, and I.

The aryl group is any one of phenyl, naphthyl, anthryl, phenanthryl, pyrenyl, thienyl, furyl, pyridyl, pyrryl.

A substituent group of the substituted aryl is any one of $C_1$-$C_8$ alkyl, $C_1$-$C_8$ alkoxy, $C_1$-$C_8$ alkylthiol, $C_1$-$C_8$ acyl, $C_1$-$C_8$ acylamino, $C_1$-$C_8$ ester, $C_1$-$C_8$ carboxyl, $C_1$-$C_8$ amido, $C_3$-$C_8$ cycloalkyl, halogen, nitryl, and nitrile.

Wherein, the $C_1$-$C_8$ alkyl is the same as mentioned above.

The $C_1$-$C_8$ alkoxy is any one of methoxy, ethoxy, n-propoxy, isopropoxy, n-butoxy, isobutoxy, sec-butoxy, tert-butoxy, n-pentyloxy, isopentyloxy, neo-pentyloxy, sec-pentyloxy, tert-pentyloxy, n-hexyloxy, isohexyloxy, neo-hexyloxy, sec-hexyloxy, tert-hexyloxy, n-heptyloxy, isoheptyloxy, neo-heptyloxy sec-heptyloxy, tert-heptyloxy, n-octyloxy, isooctyloxy, neo-octyloxy, sec-octyloxy and tert-octyloxy.

The $C_1$-$C_8$ alkyithiol is any one of methylthio, ethylthio, n-propylthio, isopropylthio, n-butylthio, isobutylthio, sec-butylthio, tert-butylthio, n-pentylthio, isopentylthio, neo-pentylthio, sec-pentylthio, tert-pentylthio, n-hexylthio, isohexylthio, neo-hexylthio, sec-hexylthio, tert-hexylthio, n-heptylthio, isoheptylthio, neo-heptylthio, sec-heptylthio, tert-heptylthio, n-octylthio, isooctylthio, neo-octylthio, sec-octylthio and tert-octylthio.

The $C_1$-$C_8$ acyl is any one of

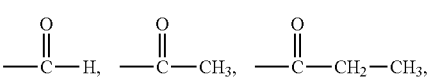

-continued

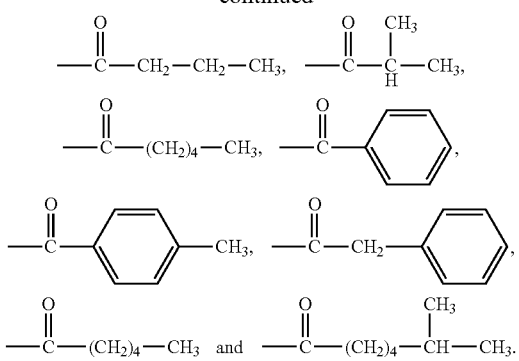

The $C_1$-$C_8$ acylamino is a group with one hydrogen absent, which has a total carbon atom number of 1-8 and acylamino

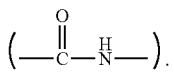

For example, the $C_1$-$C_8$ acylamino can be any one of

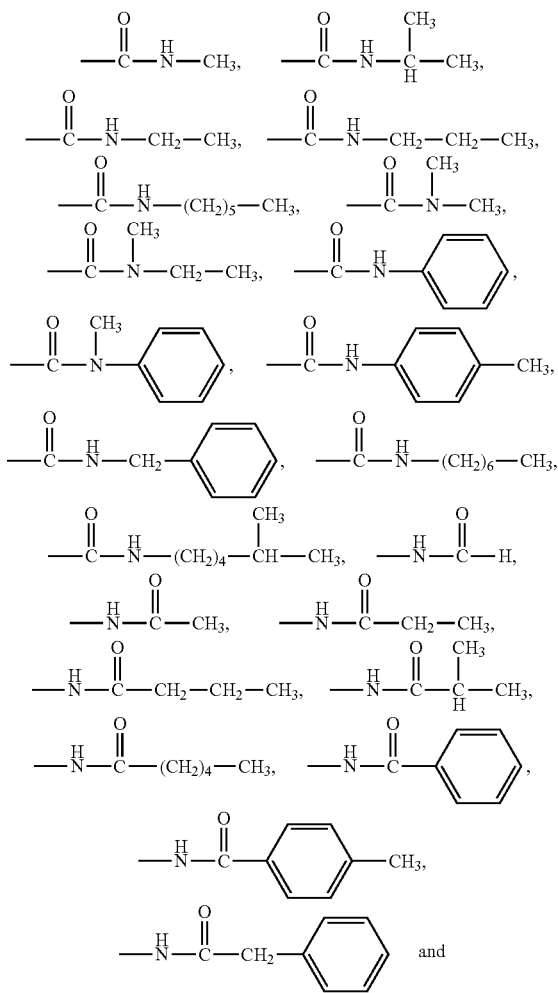

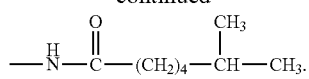

The $C_1$-$C_8$ ester is a group with one hydrogen absent, which has a total carbon atom number of 1-8 and ester

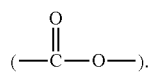

the $C_1$-$C_8$ ester is any one of

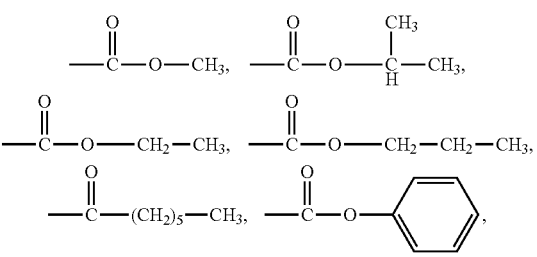

The $C_1$-$C_8$ carboxyl is a group with one hydrogen absent, which has a total carbon atom number of 1-8 and carboxyl

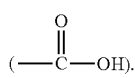

For example, the $C_1$-$C_8$ carboxyl can be any one of

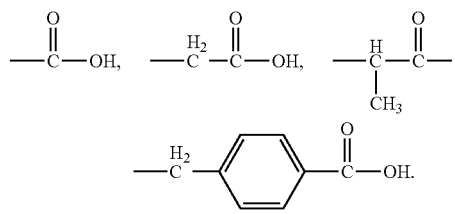

The $C_1$-$C_8$ amido is any one of methylamino, ethylamino, propylamino, butylamino, pentylamino, hexylamino, heptylamino, octylamino, dimethylamino, diethylamino, dipropylamino and dibutylamino.

The $C_3$-$C_8$ cycloalkyl is any one of cyclopropyl, cyclobutyl, cyclopentyl, cyclohexyl, cycloheptyl and cyclooctyl.

The halogen is any one of F, Cl, Br and I.

The $R_1$ is any one of nitrile group, substituted or unsubstituted $C_2$-$C_{30}$ alkynyl, substituted or unsubstituted $C_4$-$C_{30}$ multiyne, substituted or unsubstituted $C_3$-$C_{30}$ cumulene, and $R_1$ does not contain a structure unit of —C≡CCH(OH)C≡C—.

The substituted or unsubstituted $C_2$-$C_{30}$ alkynyl is any one of acetenyl,

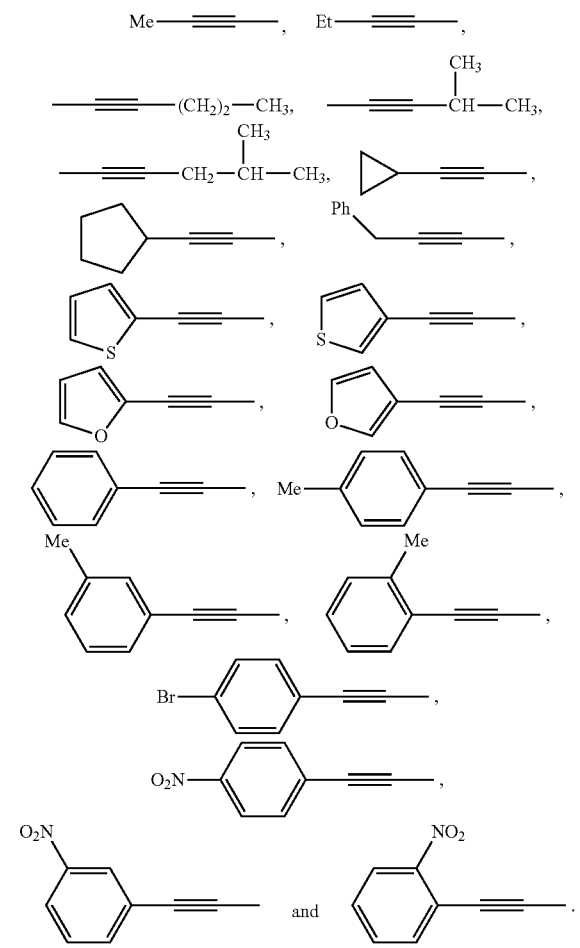

The $C_4$-$C_{30}$ multiyne is any one of

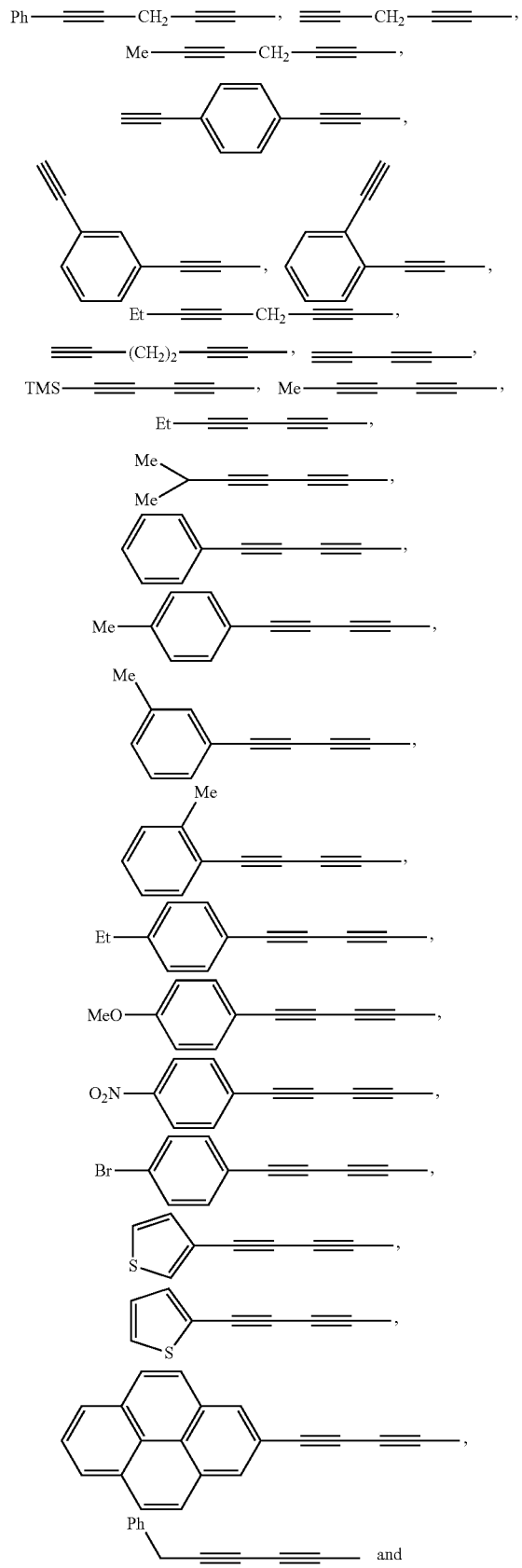

-continued

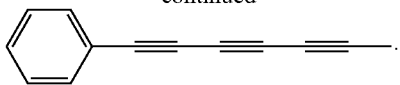

The C$_3$-C$_{30}$ cumulene is a residual alkene which contains more than one couple of adjacent carbon-carbon double bond (cumulative double bond). The C$_3$-C$_{30}$ cumulene is any one of

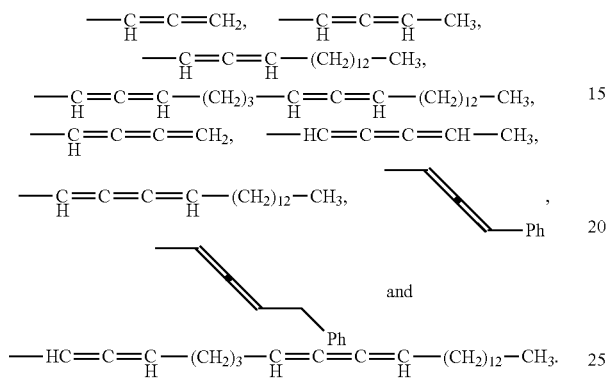

Wherein, a substituent group of the substituted or unsubstituted C$_2$-C$_{30}$ alkynyl, the substituted or unsubstituted C$_4$-C$_{30}$ multiyne, and the substituted or unsubstituted C$_3$-C$_{30}$ cumulene is any one of substituted or unsubstituted aryl, C$_1$-C$_8$ alkyl, C$_1$-C$_8$ alkoxy, C$_1$-C$_8$ alkylthiol, C$_3$-C$_8$ cycloalkyl and C$_1$-C$_8$ halogen alkyl.

The substituted or unsubstituted acyl, C$_1$-C$_8$ alkyl, C$_1$-C$_8$ alkoxy, C$_1$-C$_8$ alkylthiol, C$_3$-C$_8$ cycloalkyl is the same as mentioned above.

The C$_1$-C$_8$ alkyl halide is a substituted C$_1$-C$_8$ alkyl of which at least one hydrogen atom is substituted by at least any one of F, Cl, Br, and I.

It should be noted that the number of carbon atoms in the substituted C$_2$-C$_{30}$ alkynyl groups described herein is 2-30, excluding a number of carbon atoms in the substituent group and only including the number of carbon atoms in the alkynyl group. Similarly, any numbers of carbon atoms mentioned in the present invention refer to the number of number of carbon atoms in the group, excluding the number of carbon atoms in the substituent group.

The R$_2$ and R$_3$ are any one of hydrogen, substituted or unsubstituted aryl, substituted or unsubstituted C$_1$-C$_8$ alkyl, substituted or unsubstituted C$_1$-C$_8$ alkoxy, substituted or unsubstituted C$_1$-C$_8$ alkylthiol, substituted or unsubstituted C$_3$-C$_8$ cycloalkyl and substituted or unsubstituted C$_2$-C$_8$ alkynyl, respectively and independently. R$_2$ and R$_3$ do not contain a structure unit of —C≡CCH(OH)C≡C—.

Wherein, a substituted group of the substituted or unsubstituted C$_1$-C$_8$ alkyl, the substituted or unsubstituted C$_1$-C$_8$ alkoxy, the substituted or unsubstituted C$_1$-C$_8$ alkylthiol, the substituted or unsubstituted C$_3$-C$_8$ cycloalkyl and the substituted or unsubstituted C$_2$-C$_8$ alkynyl, is aryl or substituted aryl. The aryl or the substituted aryl is same as mentioned above.

The substituted or unsubstituted aryl, C$_1$-C$_8$ alkyl, C$_1$-C$_8$ alkoxy, C$_1$-C$_8$ alkylthiol, C$_3$-C$_8$ cycloalkyl are the same as mentioned above.

The C$_2$-C$_8$ alkynyl is any one of ethynyl, propynyl, 1-butynyl, 3-methyl-1-butynyl, 1-pentynyl, 3-methyl-1-pentynyl, 4-methyl-1-pentynyl, 1-hexynyl, 1-heptynyl, 1-octynyl and phenylethynyl.

m and n are integers from 1-6, respectively, and m+n<8. For example, under a condition of m+n<8, m and n are 1, 2, 3, 4, 5, or 6, independently and respectively. Specifically, m=1 and n=1, 2, 3, 4, 5, or 6; or m=2 and n=1, 2, 3, 4 and 5; or m=3 and n=1, 2, 3 and 4; or m=4 and n=1, 2, and 3; or m=5, n=1 or 2; or m=6, n=1.

Preferably, the X is any one of —O—, —S—, —CH$_2$—, —C(CH$_3$)$_2$—, —CHCH$_3$—, —C(COOMe)$_2$-, —C(COOEt)$_2$-, —C(COCH$_3$)(COOMe)-, —C(Cy)(COOMe)-, —C(CH$_2$CH$_2$Br)$_2$—, —C(CN)$_2$—, —C(NO$_2$)$_2$—, —SiH$_2$—, —SiMe$_2$-, —SiPh$_2$-, —NH—,

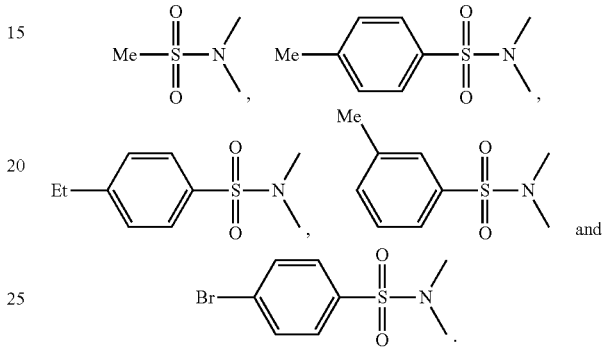

Preferably, the R$_1$ is any one of nitrile, acetenyl,

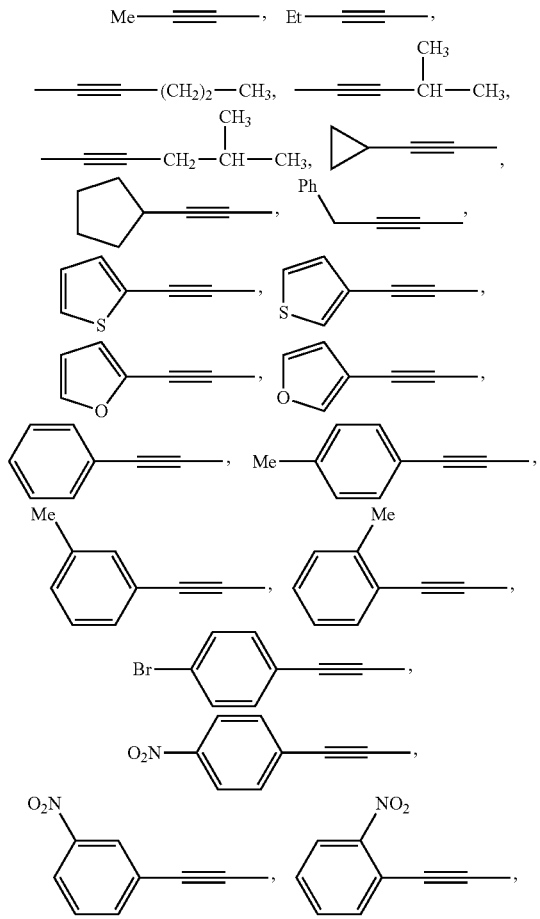

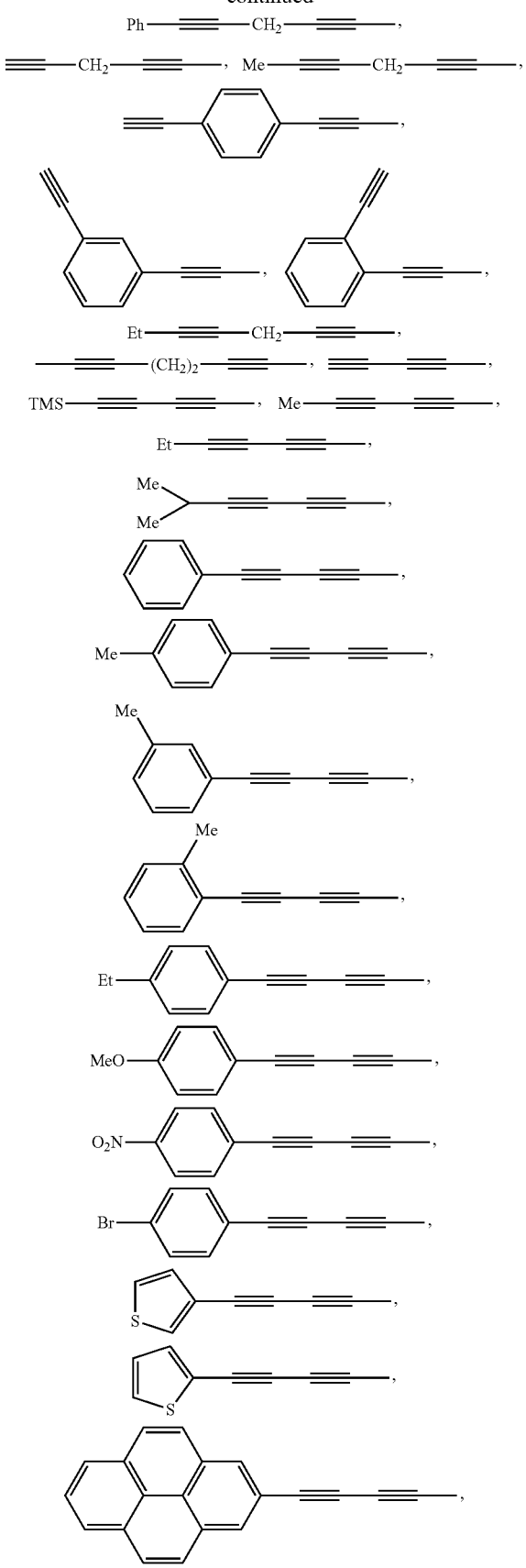
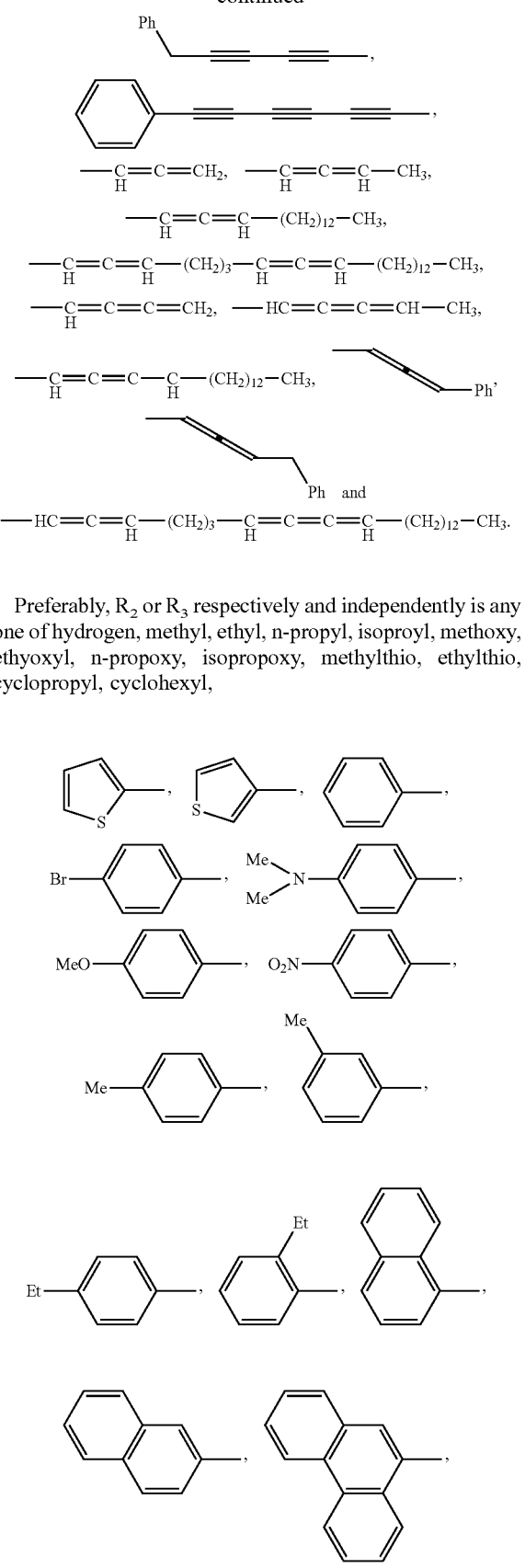
Preferably, $R_2$ or $R_3$ respectively and independently is any one of hydrogen, methyl, ethyl, n-propyl, isoproyl, methoxy, ethyoxyl, n-propoxy, isopropoxy, methylthio, ethylthio, cyclopropyl, cyclohexyl, -continued
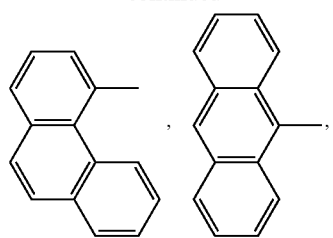
ethynyl, propynyl,
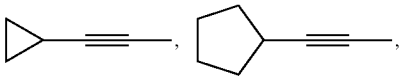
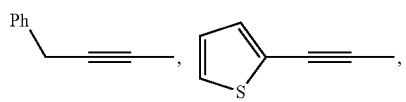
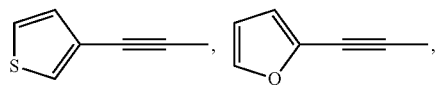
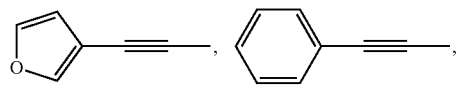
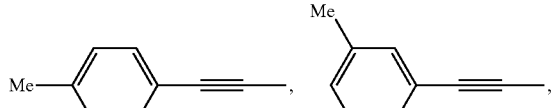
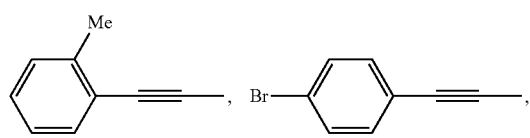
benzyl and phenethyl.
According to the present invention, preferably, the chain multiyne compound is any one of
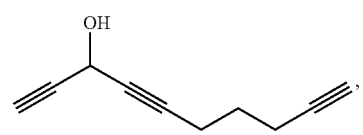
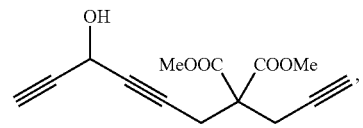
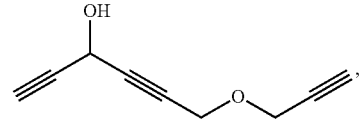
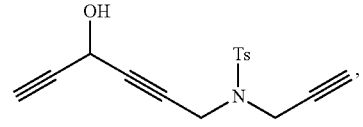
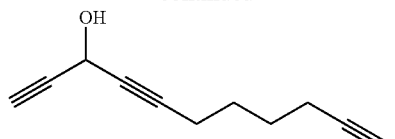
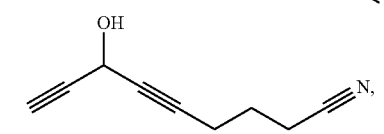
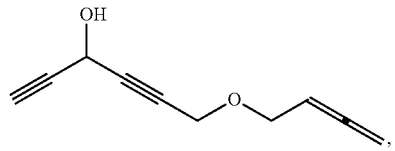
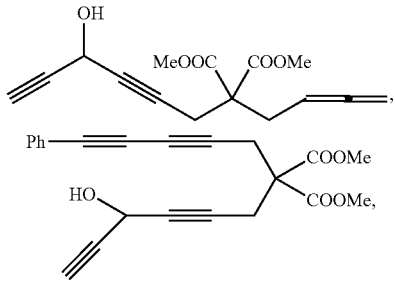
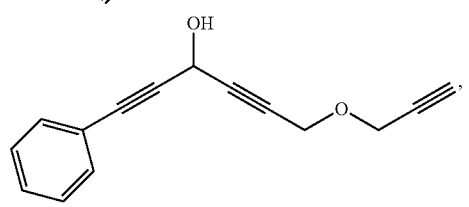
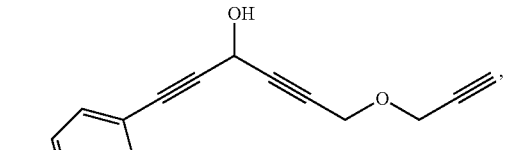
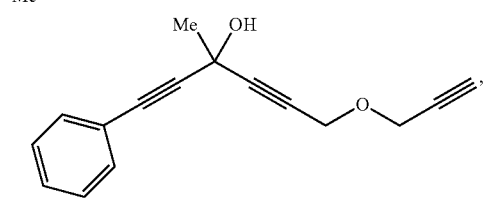
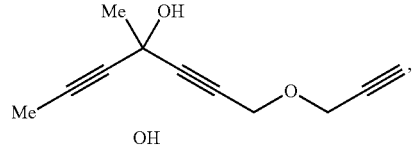
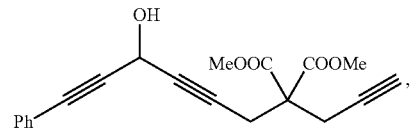
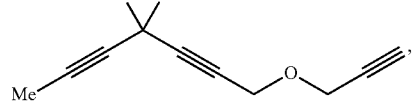

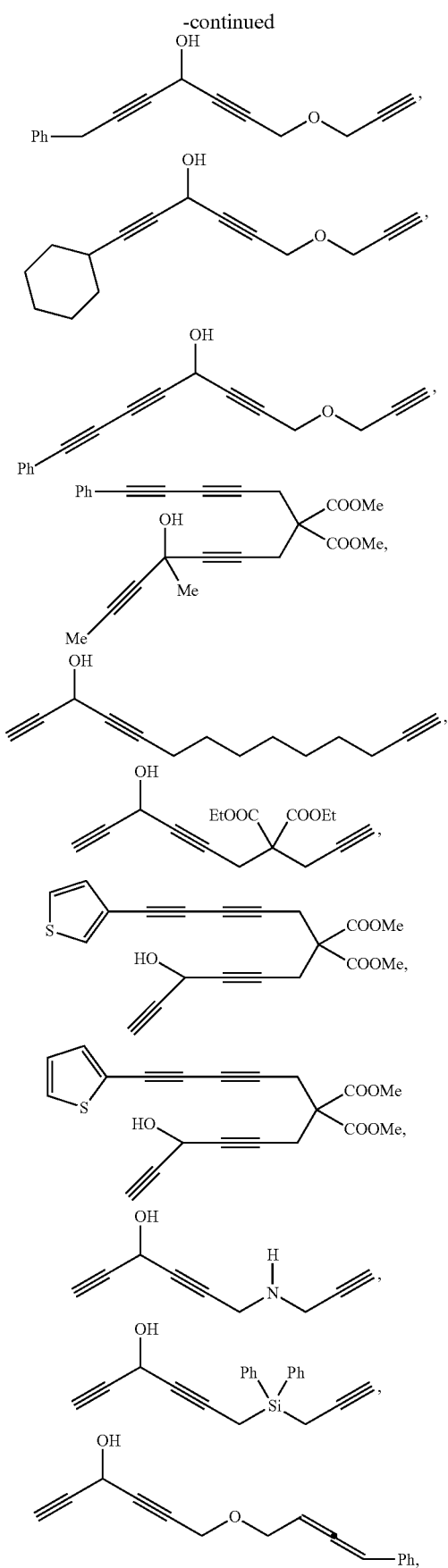
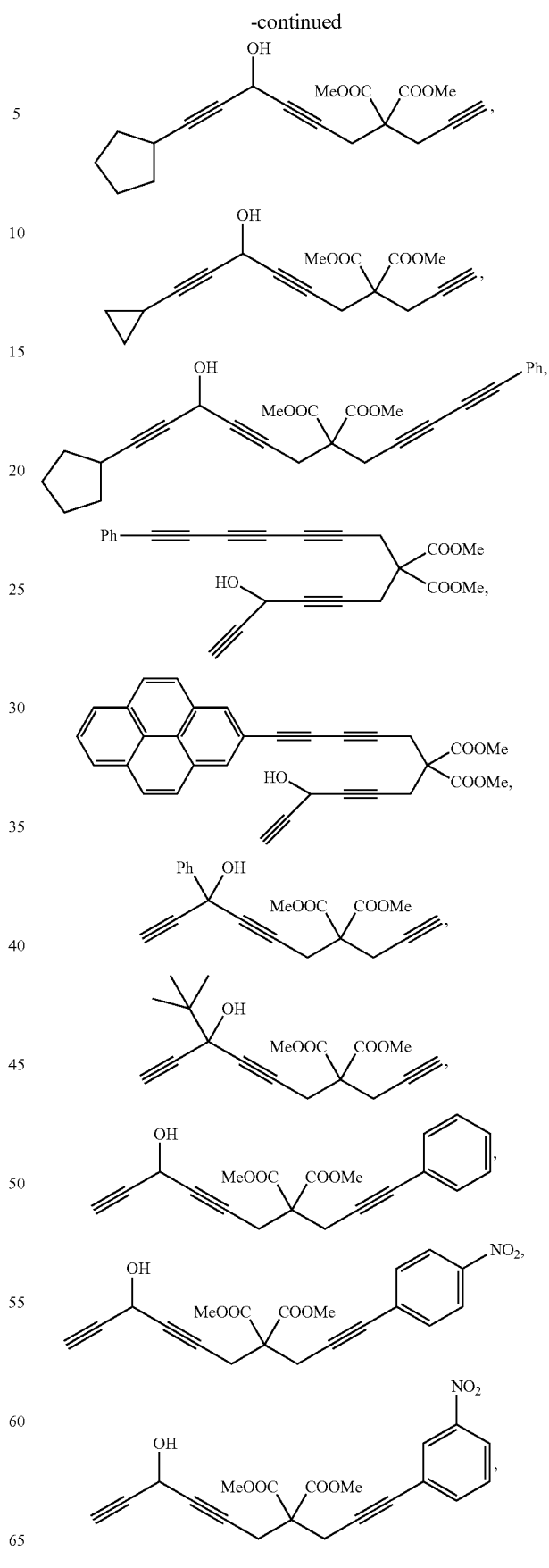

-continued

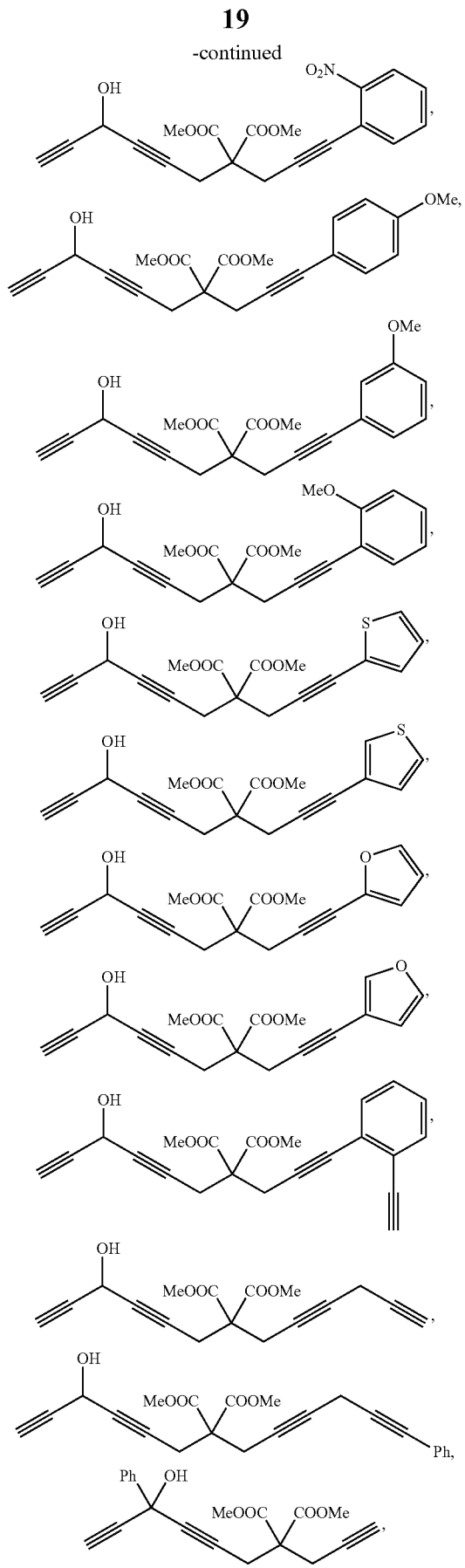

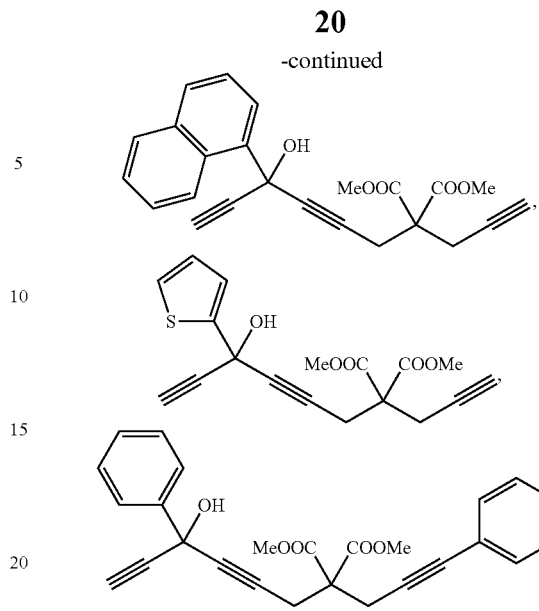

According to the second aspect of the present invention, this invention discloses a preparation method of the chain multiyne compound. When the substituent group of the chain multiyne compound $R_3$ is hydrogen, the preparation method 1 is adopted, comprising:

step a: performing a metal exchange reaction of a compound of Formula II with an organometallic reagent $RM_1$ and/or $RM_2Z$ in an aprotic solvent, and obtaining a reaction mixture;

step b: contacting and reacting the obtained reaction mixture with a compound of Formula III, obtaining a reaction mixture containing a chain multiyne compound with a protection group Y of Formula IV;

step c: taking off the protection group Y from the chain multiyne compound with a protection group Y of Formula IV of the obtained reaction mixture in step b, and obtaining the chain multiyne compound of Formula I.

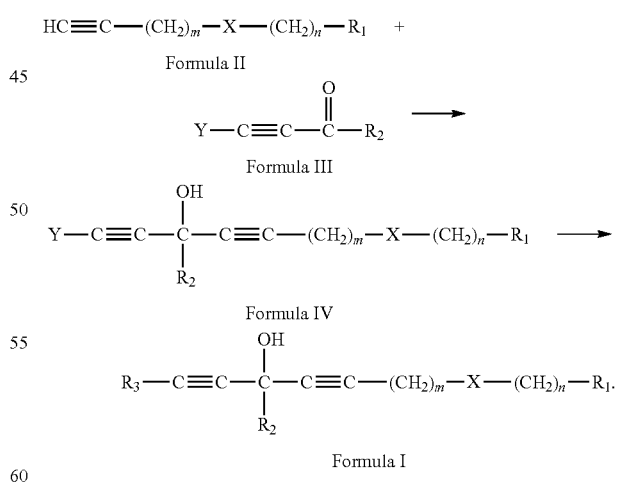

wherein, Y is a protection group to protect alkynyl, Y is any one of trimethylsilyl (TMS), triethylsilyl (TES) and triisopropylsilyl (TIPS). X, R1, m and n are respectively all the same as mentioned above.

The R of the organometallic reagent $RM_1$ and/or $RM_2Z$ is any one of $C_1$-$C_8$ alkyl, phenyl and —$NR_{10}R_{11}$. The $R_{10}$ or $R_{11}$ of —$NR_{10}R_{11}$ are any one of hydrogen, $C_1$-$C_8$ alkyl and trimethylsilyl respectively and independently. The $C_1$-$C_8$ alkyl is the same as mentioned above. $M_1$ is lithium, or sodium or potassium. $M_2$ is magnesium, Z is chlorine, or bromine or iodine. Preferably, the RM1 is at least any one of methyl lithium, ethyl lithium, n-butyl lithium, t-butyl lithium, phenyllithium, lithium diisopropylamide and lithium bis (trimethylsilyl) amide. Preferably, the $RM_2Z$ is at least any one of methylmagnesium bromide, ethylmagnesium bromide, methylmagnesium chloride and ethylmagnesium chloride.

According to the present invention, the protection group Y is deprotected from the obtained chain multiyne compound with a protection group Y of Formula IV by the deprotection agent, wherein the deprotection agent is at least one of $K_2CO_3$, $Na_2CO_3$, $Cs_2CO_3$, KF, (n-Bu)$_4$NF (tetrabutylammonium fluoride), (Et)$_4$NF (tetraethylammonium fluoride), (Me)$_4$NF (tetramethylammonium fluoride) and (n-Pr)$_4$NF (tetrapropylammonium fluoride).

According to the present invention, before the protection group Y is taken off from the obtained chain multiyne compound with a protection group Y of Formula IV by the deprotection agent, quenching and purifying processes are performed on the reaction mixture of step a which contains the chain multiyne compound with a protection group Y of Formula IV. Wherein, saturated ammonium chloride and/or water is used as a quenching agent in the quenching process. The purification process comprises extracting the chain multiyne compound with a protection group Y of Formula I by an organic solvent, drying, filtrating, concentrating, chromatographic separating the extracted organic phase, and obtaining the chain multiyne compound of Formula I. Wherein the organic solvent is at least one of diethyl ether, n-hexane, methylbenzene, 1,2-dimethoxyethane, 1,4-dioxane, dichloromethane and trichloromethaneis. The drying process on the organic phase comprises using anhydrous magnesium sulfate and/or anhydrous sodium sulfate. The chromatographic separating process on the organic phase comprises using silica gel column chromatography and/or neutral alumina.

According to the present invention, preferably, after the protection group Y is taken off from the obtained chain multiyne compound with a protection group Y of Formula IV by the deprotection agent, quenching and purifying processes are performed on the obtained mixture which contains the chain multiyne compound with a protection group Y of Formula I, the quenching and purifying processes are the same as mentioned above.

According to the second aspect of the present invention, when the $R_3$ of the chain multiyne compound of Formula I is any one of substituted or unsubstituted aryl, substituted or unsubstituted $C_1$-$C_8$ alkyl, substituted or unsubstituted $C_1$-$C_8$ alkoxy, substituted or unsubstituted $C_1$-$C_8$ alkyl sulphanyl, substituted or unsubstituted $C_3$-$C_8$ cycloalkyl and substituted or unsubstituted $C_2$-$C_8$ alkynyl, the preparation method 2 is adopted, comprising:

step a: performing a metal exchange reaction of a compound of Formula II with an organometallic reagent $RM_1$ and/or $RM_2Z$ in an aprotic solvent, and obtaining a reaction mixture containing;

step b: reacting the obtained reaction mixture with a compound of Formula V, obtaining a mixture containing the chain multiyne compound of Formula I.

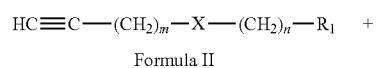

Formula II

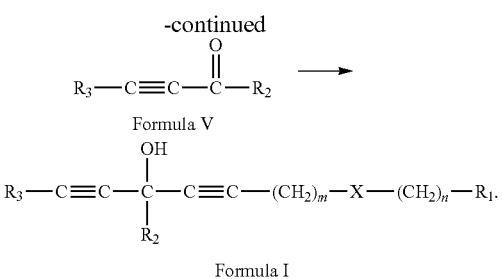

Wherein, the organometallic reagent $RM_1$ and/or $RM_2Z$ is the same as mentioned above. X, $R_1$, $R_2$, m and n are the same as mentioned above, respectively.

According to the second aspect of the present invention, there is no special quantity ratio of the compound of the Formula II to the sum of the organometallic agent $RM_1$ and/or $RM_2Z$. Preferably, the molar ratio of the compound of the Formula II to the sum of the organometallic agent $RM_1$ and/or $RM_2Z$ is 1:(0.5-1), and preferably 1:(0.9-1). When both $RM_1$ and $RM_2Z$ are comprised, there is no special quantity ratio of the compound of the Formula II to the sum of the organometallic agent $RM_1$ and/or $RM_2Z$. $RM_1$ and $RM_2Z$ can be mixed and used with any molar ratio.

According to the second aspect of the present invention, there is no special limitation on the aprotic solvent. Preferably, the aprotic solvent is at least one of benzene, methylbenzene, n-haxane, ethylether, 1,2-dimethoxyethane, tetrahydrofuran, 1,4-dioxane, petroleum ether and gasoline.

According to the second aspect of the present invention, the metal exchange reaction is performed of the compound of the Formula II and the organometallic agent $RM_1$ and/or $RM_2Z$ under protection of an inert gas. The inert gas is any gas that does not react with catalyst, raw material or product and does not have any negative effect on the reaction. The inert gas is at least one of nitrogen gas, helium gas, argon gas and neon gas. The condition of contacting the compound of the Formula II with the organometallic agent $RM_1$ and/or $RM_2Z$ in the aprotic solvent, comprises a temperature at −100-30° C., preferably at −78-0° C., with time of contact for 0.5-10 hours, preferably for 1-3 hours.

According to the second aspect of the present invention, the condition of contacting the obtained reaction mixture by contacting the compound of the Formula II with the organometallic agent $RM_1$ and/or $RM_2Z$ in an aprotic solvent with the compound of the Formula V, comprises a temperature at −100-30° C., preferably at −78-0° C., with time of contact for 0.5-10 hours, preferably for 1-5 hours.

According to the third aspect of the present invention, this invention discloses the application of the chain multiyne compound in synthesizing a fused-ring metallacyclic compound.

According to the present invention, the application of the chain multiyne compound in synthesizing a fused-ring metallacyclic compound comprises obtaining the fused-ring metallacyclic compound by reacting the chain multiyne compound with the metal complex.

According to the present invention, the metal complex is $DE_aL_b$.

Wherein, the D is any one of Fe, Co, Ni, Ru, Mn, Re, Cr, Mo, W, V, Nb, Ta, Ti, Zr, Hf, Rh, Pd, Ir, Pt and Os.

The E is any one of H, F, Cl, Br, I, SCN and CN.

The L is any one of a phosphine ligand, a CO ligand, a pyridine ligand, a N-heterocyclic carbene ligand, a nitrile ligand and an isocyanoid ligand.

Preferably, the L is any one of trimethylphosphine, triethylphosphine, tripropylphosphine, triisopropylphosphine, tritertbutylphosphine, tricyclohexylphosphine, triphenylphosphine, methylpyridine, ethylpyridine, 1,4-bipyridine, 1,2-bis(4-pyridyl)ethylene, vinylpyridine, pyridine-3-boronic acid, aminopyridine, cyanopyridine, pyridinethiol, ethynylpyridine, dimethylaminopyridine, ethylene pyridine, phenylpyridine, 1,2-bis(4-pyridyl)ethane, imidazole N-heterocyclic carbene, imidazoline N-heterocyclic carbene, thiazole N-heterocyclic carbene, triazole N-heterocyclic carbene, acetonitrile, propionitrile, benzonitrile, cyclohexylisocyanide, tert-butylisocyanide and phenylisocyanide.

The a and b are integers from 0-6, respectively; when a≥2, E is different or is the same and when b≥2, L is different or is the same.

Preferably, the metal complex is any one of $OsCl_2(PPh_3)_3$, $RuCl_2(PPh_3)_3$, $RhCl(PPh_3)_3$ and $IrHCl_2(PPh_3)_3$.

The present invention is hereinafter described in details by specific embodiments.

Embodiment 1

The present embodiment is to prepare the chain multiyne compound disclosed in the present invention.

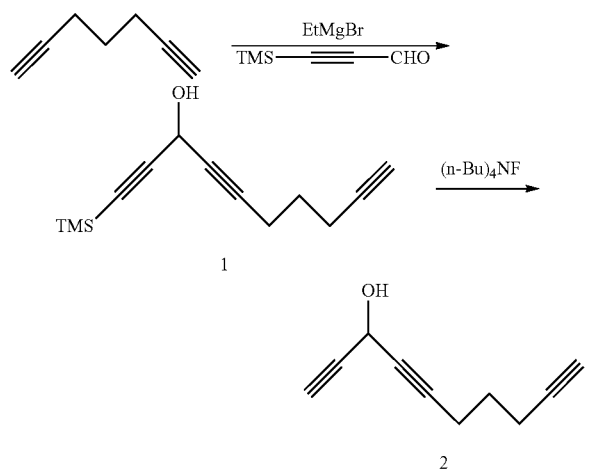

Wherein, TMS represents trimethylsilyl, EtMgBr is ethylmagnesium bromide (purchased from J & K Technology Co., Ltd., and a trademark number is 248474),

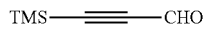

is 3-trimethylsilylpropynal (purchased from J & K Technology Co., Ltd., and a trademark number is 2975-46-4), (n-Bu)$_4$NF is tetrabutylammonium fluoride (purchased from J & K Technology Co., Ltd., and a trademark number is A10588).

Step 1. The Preparation of the Compound 1 (See Above)

1,6-heptadiyne (5.0 mL, 4.02 g, 43.63 mmol, purchased from Aladdin Reagent (Shanghai) Co., Ltd., and a trademark number is H102744-25 mL) was dissolved into 100 mL tetrahydrofuran under an atmosphere of N2 and magnetic stirring.

The solution was cooled to 0° C., a solution of ethylmagnesium bromide (1.0 M tetrahydrofuran solution, 43.6 mL, and containing ethylmagnesium bromide 43.60 mmol) was added gradually within 1 h.

The solution reacted for another 1 h at room temperature and then cooled to 0° C.

Trimethylsilylpropynal (7.30 mL, 43.60 mmol) was added rapidly and reacted for 1 h.

After reaction, the solution was quenched with saturated ammonium chloride, and the solution was extracted with diethyl ether.

The organic phase was merged and the organic phase was dried with anhydrous magnesium sulfate.

The organic solution was filtrated, concentrated to dryness. The residue was chromatographed with silica gel (eluent: n-hexane:ethyl acetate=6:1 (v/v)) to obtain 5.71 g compound 1 as colorless oily liquid. A yield is 60%. (The yield of compound 1 is calculated as a molar amount of the compound 1 divided by a molar amount of 1,6-heptanedyne×100%.)

NMR data and high resolution mass spectrometry data of the compound 1 are as follows.

$^1$H NMR δ=5.04 (t, J=1.80 Hz, 1H), 2.69 (br, 1H), 2.31 (td, J=6.99 Hz, J=1.80 Hz, 2H), 2.25 (td, J=6.99 Hz, J=2.60 Hz, 2H), 1.93 (t, J=2.60 Hz, 1H), 1.69 (m, 2H), 0.14 (s, 9H); $^{13}$C NMR δ=102.71, 88.81, 84.24, 83.45, 78.31, 69.12, 52.59, 27.25, 17.82, 17.56, −0.26. HRMS-ESI (m/z) calculated value $C_{13}H_{18}OSiNa$ [M+Na]$^+$ 241.1019, measured value 241.1025.

Step 2. The Preparation of the Compound 2 (See Above).

The compound 1 (5.0 g, 22.90 mmol) was dissolved into 120 mL tetrahydrofuran.

The solution was cooled to 0° C. A solution of tetrabutylammonium fluoride (1.0 M tetrahydrofuran solution, 27.48 mL, containing tetrabutylammonium fluoride 27.48 mmol) was slowly added.

The reaction was stopped until the raw materials disappeared (about 30 min).

The reaction solution was quenched with saturated ammonium chloride, and then extracted with diethyl ether.

The organic phase was merged and the organic phase was dried with anhydrous magnesium sulfate.

The organic solution was filtrated, concentrated to dryness. The residue was chromatographed with silica gel (eluent: n-hexane/ethyl acetate with a volume ratio of 4/1) to obtain 2.85 g compound 2 as colorless oily liquid. Yield is 85%. (The yield of compound 2 is calculated as a molar amount of the compound 2 divided by a molar amount of the compound 1×100%.)

NMR data and high resolution mass spectrometry data of the compound 2 are as follows.

$^1$H NMR δ=5.08 (m, 1H), 2.69 (br, 1H), 2.53 (t, J=2.20 Hz, 1H), 2.34 (td, J=7.00 Hz, J=1.85 Hz, 2H), 2.25 (td, J=7.00 Hz, J=2.57 Hz, 2H), 1.95 (t, J=2.57 Hz, 1H), 1.71 (m, 2H); $^{13}$C NMR δ=84.65, 83.49, 81.52, 77.91, 72.39, 69.22, 52.06, 27.18, 17.77, 17.62. HRMS-ESI (m/z) calculated value $C_{10}H_{10}OSiNa$ [M+Na]$^+$ 169.0624, measured value 169.0651.

Embodiment 2

The present embodiment is to prepare the chain multiyne compound disclosed in the present invention.

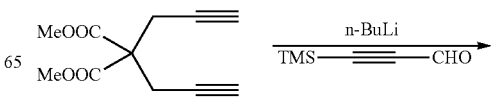

-continued

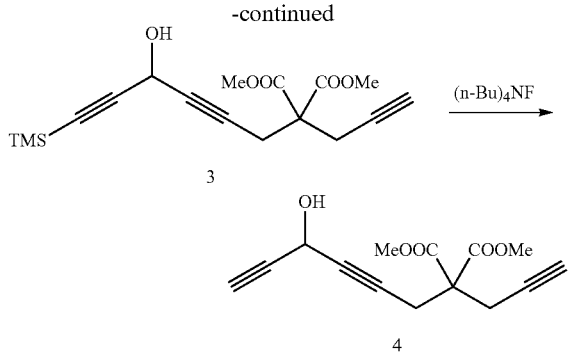

Wherein, n-BuLi represents n-butyllithium (purchased from J & K Technology Co., Ltd., and a trademark number is 913796).

Step 1. The Preparation of the Compound 3 (See Above)

2,2-dimethyl dipropargylmalonate (5.0 g, 24.0 mmol, synthesized according to literature *J. Am. Chem. Soc.* 2013, 135, 8133.) was dissolved into 200 mL tetrahydrofuran under an atmosphere of $N_2$ and magnetic stirring.

The solution was cooled to −78° C., n-butyllithium (2.2 M tetrahydrofuran solution, 10.90 mL, containing n-butyllithium 24.0 mmol) was added gradually for 1 h.

The solution reacted at −78° C. for 15 mins.

Trimethylsilylpropynal (3.52 mL, 24.0 mmol) was added rapidly and reacted for 2 h.

After reaction, the solution was quenched with saturated ammonium chloride, and the solution was extracted with diethyl ether.

The organic phase was merged and the organic phase was dried with anhydrous magnesium sulfate.

The organic solution was filtered, concentrated to dryness. The residue was chromatographed with silica gel (eluent: n-hexane:ethyl acetate=5:1 (v/v)) to obtain 4.82 g compound 3 as light yellow oily liquid. The yield is 60%. (The yield of compound 3 is calculated as a molar amount of the compound 3 divided by a molar amount of 2,2-dimethyl dipropargylmalonate×100%.)

NMR data and high resolution mass spectrometry data of the compound 3 are as follows.

$^1$H NMR δ=5.03 (s, 1H), 3.76 (s, 6H), 3.03 (d, J=2.00 Hz, 2H), 2.97 (d, J=2.64 Hz, 2H), 2.37 (br, 1H), 2.03 (t, J=2.60 Hz, 1H), 0.19 (s, 9H); $^{13}$C NMR δ=169.05, 102.11, 88.97, 81.08, 79.06, 78.28, 71.88, 56.59, 53.14, 52.30, 22.93, 22.77, −0.41; HRMS-ESI (m/z) calculated value $C_{17}H_{22}O_5SiNa$ [M+Na]$^+$357.1129, measured value 357.1130.

Step 2. The Preparation of the Compound 4 (See Above).

The compound 3 (4.82 g, 14.4 mmol) was dissolved into 150 mL tetrahydrofuran.

The solution was cooled to −30° C., a solution of tetrabutylammonium fluoride (1.0 M tetrahydrofuran solution, 21.6 mL, containing tetrabutylammonium fluoride 21.6 mmol) was added slowly.

The solution reacted until the raw materials disappear (about 20 min).

The reacted solution was quenched with saturated ammonium chloride, and the solution was extracted with diethyl ether. The organic phase was dried with anhydrous magnesium sulfate.

The organic solution was filtered, concentrated to dryness. The residue was chromatographed with silica gel (eluent: n-hexane:ethyl acetate=3:1 (v/v)) to obtain 3.21 g compound 4 as light yellow oily liquid. Yield is 85%. (The yield of compound 4 is calculated as a molar amount of the compound 4 divided by a molar amount of the compound 4×100%.)

NMR data and high resolution mass spectrometry data of the compound 4 are as follows.

$^1$H NMR δ=5.05 (ddt, J=7.51 Hz, J=2.25 Hz, J=2.11 Hz, 1H), 3.76 (s, 1H), 3.02 (d, J=2.11 Hz, 2H), 2.95 (d, J=2.72 Hz, 2H), 2.81 (d, J=7.51 Hz, 1H), 2.53 (d, J=2.25 Hz, 1H), 2.03 (t, J=2.68 Hz, 1H); $^{13}$C NMR δ=169.11, 80.99, 80.78, 79.03, 78.19, 72.44, 72.10, 56.48, 53.25, 51.54, 22.84, 22.75; HRMS-ESI (m/z) calculated value $C_{14}H_{14}O_5Na$ [M+Na]$^+$ 285.0733, measured value 285.0734.

Embodiment 3

The present embodiment is to prepare the chain multiyne compound disclosed in the present invention.

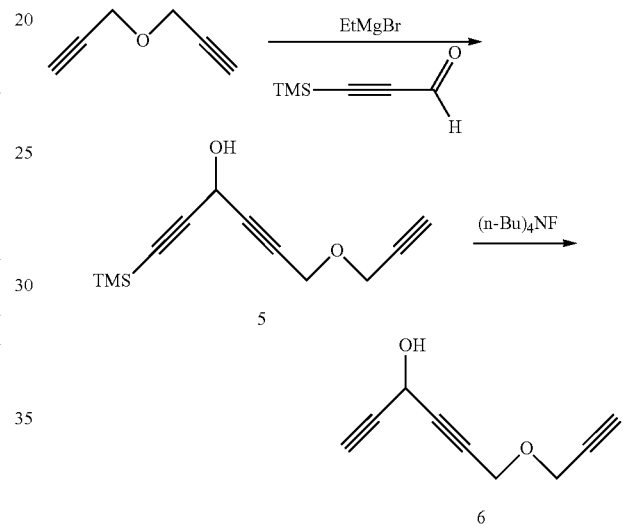

Step 1. The Preparation Method of Compound 5 is the Same as that of Compound 1, Except the Following Characteristics:

the 1,6-heptadiyne used in embodiment 1 is replaced by dipropargyl ether (purchased from Alfa Aesar (China) Chemical Co., Ltd., and a trademark number is MFCD00048108) with an equal molar amount.

Yield of compound 5 is 75%. The yield of compound 5 is calculated as a molar amount of the compound 5 divided by a molar amount of dipropargyl ether×100%.

NMR data and high resolution mass spectrometry data of the compound 5 are as follows.

$^1$H NMR δ=5.14 (t, J=1.67 Hz, 1H), 4.31 (d, J=1.67 Hz, 1H), 4.24 (b, J=2.37 Hz, 2H), 2.47 (br, 1H), 2.46 (t, J=2.37 Hz, 1H), 0.17 (s, 9H); $^{13}$C NMR δ=101.60, 89.95, 84.19, 79.74, 78.85, 75.40, 56.81, 56.75, 52.59, −0.22; HRMS-ESI (m/z) calculated value $C_{12}H_{16}O_2SiNa$ [M+Na]$^+$ 243.0812, measured value 248.0805.

Step 2. The Preparation Method of Compound 6 is the Same as that of Compound 2, Except the Following Characteristics:

the compound 1 in step 2 of embodiment 1 is replaced by the compound 5 in step 1 of the present embodiment.

The yield of the compound 6 is 87%. (The yield of compound 6 is calculated as a molar amount of the compound 6 divided by a molar amount of the compound 5×100%.)

NMR data and high resolution mass spectrometry data of the compound 6 are as follows.

$^1$H NMR δ=5.16 (s, 1H), 2.69 (br, 1H), 4.31 (d, J=1.52 Hz, 1H), 4.25 (d, J=2.25 Hz, 2H), 2.80 (br, 2H), 2.57 (d, J=2.25 Hz, 1H), 2.47 (t, J=2.25 Hz, 1H); $^{13}$C NMR δ=83.81, 80.69, 80.09, 78.82, 75.47, 73.13, 56.87, 56.76, 52.05; HRMS-ESI (m/z) calculated value $C_9H_8O_2Na$ [M+Na]$^+$ 171.0417, measured value 171.0411.

Embodiment 4

The present embodiment is to prepare the chain multiyne compound disclosed in the present invention.

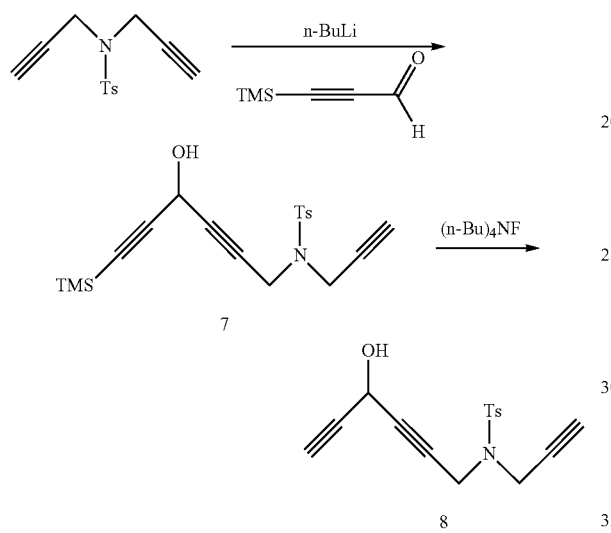

Step 1. The Preparation Method of Compound 7 is the Same as that of Compound 1, Except the Following Characteristics:

the 1,6-heptadiyne used in embodiment 1 is replaced by N,N-Dipropargyl-p-toluenesulfonamide (synthesized according to literature *J. Am. Chem. Soc.* 2000, 122, 11529.) with an equal molar amount.

Yield of compound 7 is 60%. The yield of compound 7 is calculated as a molar amount of the compound 7 divided by a molar amount of N,N-Dipropargyl-p-toluenesulfonamide× 100%.

NMR data and high resolution mass spectrometry data of the compound 7 are as follows.

$^1$H NMR δ=7.64 (d, J=12.34 Hz, 2H), 7.35 (d, J=12.34 Hz, 2H), 5.16 (t, J=1.64 Hz, 1H), 3.95 (d, J=1.64 Hz, 2H), 3.87 (d, J=2.37 Hz, 2H), 2.65 (br, 1H), 2.49 (t, J=2.37 Hz, 1H), 2.34 (s, 3H), 0.13 (s, 9H); $^{13}$C NMR δ=137.50, 136.79, 129.87, 128.37, 102.50, 87.85, 84.11, 80.74, 78.64, 74.80, 52.64, 34.83, 34.55, 21.56, −0.32; HRMS-ESI (m/z) calculated value $C_{19}H_{23}NSO_3SiNa$ [M+Na]$^+$ 396.1060, measured value 396.1058.

Step 2. The Preparation Method of Compound 8 is the Same as that of Compound 2, Except the Following Characteristics.

The compound 1 in step 2 of embodiment 1 is replaced by the compound 7 in step 1 of the present embodiment.

The yield of the compound 8 is 81%. The yield of compound 8 is calculated as a molar amount of the compound 8 divided by a molar amount of the compound 7×100%.

NMR data and high resolution mass spectrometry data of the compound 8 are as follows.

$^1$H NMR δ=7.63 (d, J=12.37 Hz, 2H), 7.32 (d, J=12.37 Hz, 2H), 5.19 (dt, J=2.35 Hz, J=1.64 Hz, 1H), 3.93 (d, J=1.64 Hz, 2H), 3.85 (d, J=2.36 Hz, 2H), 2.55 (br, 1H), 2.52 (d, J=2.35 Hz, 1H), 2.47 (t, J=2.36 Hz, 1H), 2.33 (s, 3H); $^{13}$C NMR δ=137.48, 136.72, 129.77, 128.27, 87.835, 84.01, 80.33, 78.54, 74.58, 72.76, 52.53, 34.92, 34.48, 21.57; HRMS-ESI (m/z) calculated value $C_{16}H_{15}NSO_3Na$ [M+Na]$^+$ 324.0665, measured value 324.0661.

Embodiment 5

The present embodiment is to prepare the chain multiyne compound disclosed in the present invention.

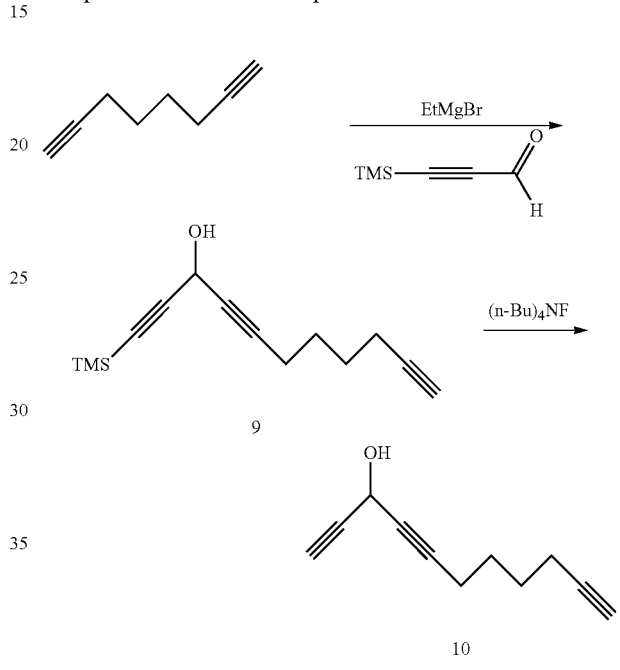

Step 1. The Preparation Method of Compound 9 is the Same as that of Compound 1, Except:

the 1,6-heptadiyne used in embodiment 1 is replaced by 1,7-octadiyne (purchased from Alfa Aesar (China) Chemical Co., Ltd., and a trademark number is MFCD0000880) with an equal molar amount.

The yield of compound 9 is 45%. The yield of compound 9 is calculated as a molar amount of the compound 9 divided by a molar amount of 1,7-octadiyne×100%.

NMR data and high resolution mass spectrometry data of the compound 9 are as follows.

$^1$H NMR δ=5.07 (t, J=1.97 Hz, 1H), 2.55 (br, 1H), 2.25 (td, J=7.00 Hz, J=1.85 Hz, 2H), 2.20 (td, J=7.00 Hz, J=2.80 Hz, 2H), 1.95 (t, J=2.51 Hz, 1H), 1.63 (m, 4H), 0.17 (s, 9H); $^{13}$C NMR δ=102.62, 88.75, 84.91, 84.06, 77.82, 68.67, 52.55, 27.40, 27.13, 18.22, 17.09, −0.33; HRMS-ESI (m/z) calculated value $C_{14}H_{20}OSiNa$ [M+Na]$^+$ 255.1176, measured value 255.1152.

Step 2. The Preparation Method of Compound 10 is the Same as that of Compound 2, Except the Following Characteristics:

the compound 1 in step 2 of embodiment 1 is replaced by the compound 9 in step 1 of the present embodiment.

The yield of the compound 10 is 78%. The yield of compound 10 is calculated as a molar amount of the compound 10 divided by a molar amount of the compound 9×100%.

NMR data and high resolution mass spectrometry data of the compound 10 are as follows.

$^1$H NMR δ=5.08 (d, J=2.20 Hz, 1H), 2.90 (br, 1H), 2.54 (d, J=2.25 Hz, 1H), 2.23 (td, J=6.57 Hz, J=1.97 Hz, 2H), 2.19 (td, J=6.65 Hz, J=2.54 Hz, 2H, 2H), 1.95 (d, J=2.59 Hz, 1H), 1.60 (m, 4H); $^{13}$C NMR δ=85.21, 84.14, 76.83, 72.28, 68.77, 51.91, 27.38, 27.10, 18.15, 17.88; HRMS-ESI (m/z) calculated value $C_{11}H_{12}ONa$ [M+Na]$^+$ 183.0780, measured value 183.0785.

Embodiment 6

The present embodiment is to prepare the chain multiyne compound disclosed in the present invention.

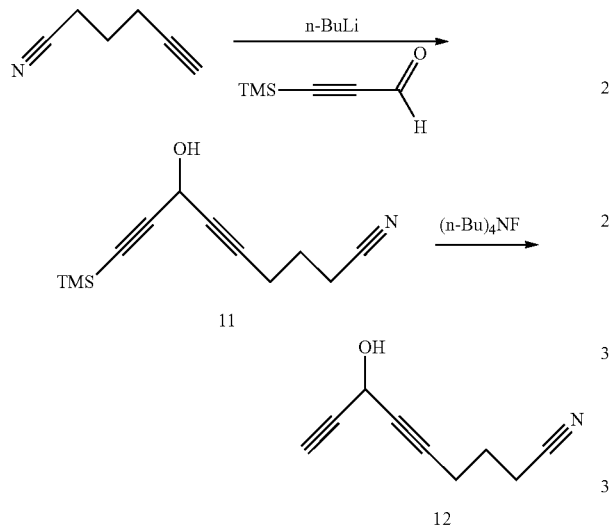

11

12

Step 1. The Preparation Method of Compound 11 is the Same as that of Compound 3, Except the Following Characteristics:

the 2,2-dimethyl dipropargylmalonate used in embodiment 2 is replaced by 5-cyano-1-pentyne (purchased from J & K Technology Co., Ltd., and a trademark number is 009109) with an equal molar amount.

The compound 11 is light yellow oily liquid. The yield of compound 11 is 81%. The yield of compound 11 is calculated as a molar amount of the compound 11 divided by a molar amount of 5-cyano-1-pentyne×100%.

NMR data and high resolution mass spectrometry data of the compound 11 are as follows.

$^1$H NMR δ=5.07 (t, J=1.85 Hz, 1H), 2.54 (br, 1H), 2.48 (t, J=7.08 Hz, 2H), 2.41 (td, J=6.74 Hz, J=1.85 Hz, 2H), 1.87 (tt, J=7.08 Hz, J=6.74 Hz, 2H), 0.17 (s, 9H); $^{13}$C NMR δ=119.23, 102.22, 89.39, 82.51, 79.59, 52.60, 24.29, 17.99, 16.23, −0.22. HRMS-ESI (m/z) calculated value $C_{12}H_{17}NOSiNa$ [M+Na]$^+$ 242.0972, measured value 242.0968.

Step 2. The Preparation Method of Compound 12 is the Same as that of Compound 4, Except the Following Characteristics:

the compound 3 in step 2 of embodiment 2 is replaced by the compound 11 in step 1 of the present embodiment.

The compound 12 is light yellow oily liquid. Yield of the compound 12 is 87%. The yield of compound 12 is calculated as a molar amount of the compound 12 divided by a molar amount of the compound 11×100%.

NMR data and high resolution mass spectrometry data of the compound 12 are as follows.

$^1$H NMR δ=5.09 (dd, J=2.00 Hz, J=1.70 Hz, 1H), 2.65 (br, 1H), 2.56 (d, J=2.00 Hz, 1H), 2.49 (t, J=7.13 Hz, 2H), 2.42 (td, J=6.73 Hz, J=1.70 Hz, 2H), 1.88 (tt, J=7.13 Hz, J=6.73 Hz, 1H); $^{13}$C NMR δ=119.28, 82.79, 81.24, 79.25, 72.63, 52.01, 24.21, 17.94, 16.29. HRMS-ESI (m/z) calculated value $C_9H_9NONa$ [M+Na]$^+$ 170.0576, measured value 170.0583.

Embodiment 7

The present embodiment is to prepare the chain multiyne compound disclosed in the present invention.

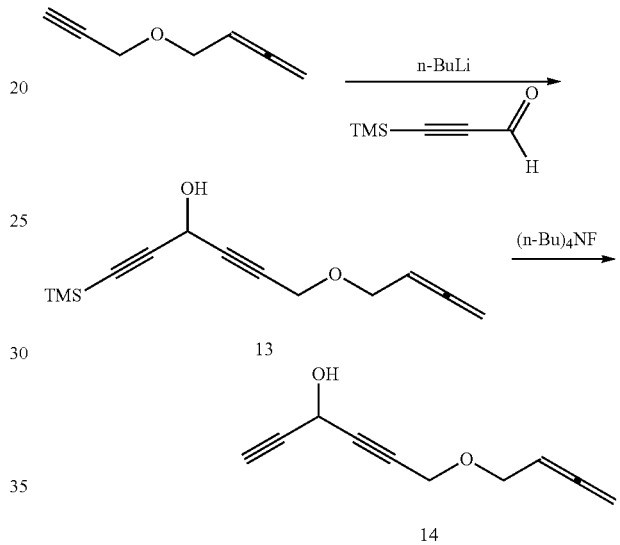

13

14

Step 1. The Preparation Method of Compound 13 is the Same as that of Compound 3, Except the Following Characteristics:

the 2,2-dimethyl dipropargylmalonate used in embodiment 2 is replaced by 4-propargyloxy-1,2-butadiene (synthesized according to literature *Eur J. Org. Chem.* 2013, 15, 3041, and PCT Int. Appl., 2011050016) with an equal molar amount.

The compound 13 is light yellow oily liquid. The yield of compound 13 is 55%. The yield of compound 13 is calculated as a molar amount of the compound 13 divided by a molar amount of 4-propargyloxy-1,2-butadiene×100%.

NMR data and high resolution mass spectrometry data of the compound 13 are as follows.

$^1$H NMR δ=5.20 (tt, J=6.69 Hz, J=6.69 Hz, 1H), 5.15 (t, J=1.84 Hz, 1H), 4.78 (dt, J=6.69 Hz, J=2.34 Hz, 2H), 4.23 (d, J=1.84 Hz, 2H), 4.12 (dt, J=6.69 Hz, J=2.34 Hz, 2H), 2.68 (br, 1H), 0.11 (s, 9H); $^{13}$C NMR δ=209.36, 101.23, 86.51, 83.24, 80.67, 80.12, 75.67, 72.53, 67.32, 56.91, 52.35; HRMS-ESI (m/z) calculated value $C_{13}H_{18}O_2SiNa$ [M+Na]$^+$ 257.0968, measured value 257.0986.

Step 2. The Preparation Method of Compound 14 is the Same as that of Compound 4, Except the Following Characteristics:

the compound 3 in step 2 of embodiment 2 is replaced by the compound 13 in step 1 of the present embodiment.

The compound 14 is light yellow oily liquid. The yield of the compound 14 is 87%. The yield of compound 14 is calculated as a molar amount of the compound 14 divided by a molar amount of the compound 13×100%.

NMR data and high resolution mass spectrometry data of the compound 14 are as follows.

$^1$H NMR δ=5.22 (tt, J=6.71 Hz, J=6.71 Hz, 1H), 5.16 (dt, J=1.84 Hz, J=1.84, 1H), 4.81 (dt, J=6.71 Hz, J=2.35 Hz, 2H), 4.23 (d, J=1.84 Hz, 2H), 4.09 (dt, J=6.71 Hz, J=2.35 Hz, 2H), 2.71 (br, 1H), 2.57 (d, J=1.84 Hz, 1H); $^{13}$C NMR δ=209.57, 86.81, 83.45, 80.77, 80.13, 76.01, 72.81, 67.46, 56.81, 51.50; HRMS-ESI (m/z) calculated value $C_{10}H_{10}O_2Na$ [M+Na]$^+$ 185.0573, measured value 185.0574.

Embodiment 8

The present embodiment is to prepare the chain multiyne compound disclosed in the present invention.

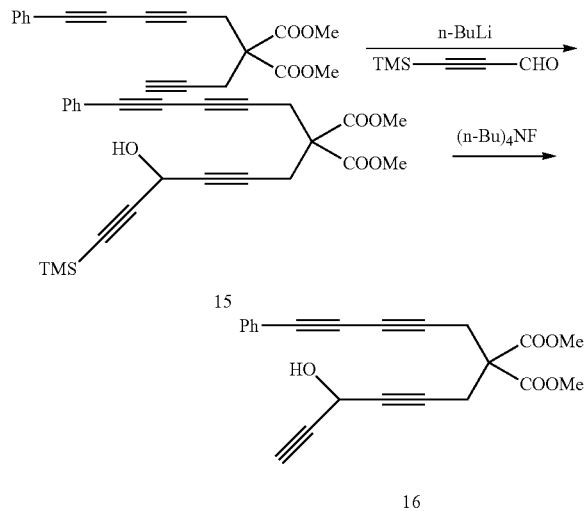

Step 1. The Preparation Method of Compound 15 is the Same as that of Compound 3, Except the Following Characteristics:

the 2,2-dimethyl dipropargylmalonate used in embodiment 2 is replaced by 2-propargyl-2-(5-phenyl-2,4-pentadiynyl) dimethyl malonate (synthesized according to literature *J. Am. Chem. Soc.* 2008, 130, 14713.) with an equal molar amount.

The compound 15 is light yellow oily liquid. Yield of compound 15 is 45%. The yield of compound 15 is calculated as a molar amount of the compound 15 divided by a molar amount of 2-propargyl-2-(5-phenyl-2,4-pentadiynyl) dimethyl malonate×100%.

NMR data and high resolution mass spectrometry data of the compound 15 are as follows.

$^1$H NMR δ=7.30-7.48 (m, 5H), 5.04 (dt, J=7.61 Hz, J=2.02 Hz, 1H), 3.79 (s, 6H), 3.16 (s, 2H), 3.07 (d, J=2.02 Hz, 2H), 2.35 (d, J=7.61 Hz, 1H), 0.19 (s, 9H); $^{13}$C NMR δ=168.86, 132.57, 129.16, 128.56, 101.99, 89.28, 81.30, 79.12, 77.82, 75.92, 68.30, 56.73, 53.29, 52.45, 24.06, 23.29, –0.36; HRMS-ESI (m/z) calculated value $C_{25}H_{26}O_5SiNa$ [M+Na]$^+$ 457.1442, measured value 457.1450.

Step 2. The Preparation Method of Compound 16 is the Same as that of Compound 4, Except the Following Characteristics:

the compound 3 in step 2 of embodiment 2 is replaced by the compound 15 in step 1 of the present embodiment.

The compound 16 is light yellow solid. Yield of the compound 16 is 89%. The yield of compound 16 is calculated as a molar amount of the compound 16 divided by a molar amount of the compound 15×100%.

NMR data and high resolution mass spectrometry data of the compound 16 are as follows.

$^1$H NMR δ=7.29-7.48 (m, 5H), 5.07 (dt, J=2.25, J=2.29, 1H), 3.80 (s, 6H), 3.16 (s, 2H), 3.07 (d, J=2.29 Hz, 2H), 2.55 (d, J=2.25 Hz, 1H), 2.19 (br, 1H); $^{13}$C NMR δ=168.89, 132.59, 129.20, 128.40, 121.52, 80.93, 79.33, 77.74, 75.99, 73.78, 72.56, 68.37, 56.67, 53.39, 51.86, 24.10, 23.25; HRMS-ESI (m/z) calculated value $C_{22}H_{18}O_5Na$ [M+Na]$^+$ 385.1046, measured value 385.1049.

Embodiment 9

The present embodiment is to prepare the chain multiyne compound disclosed in the present invention.

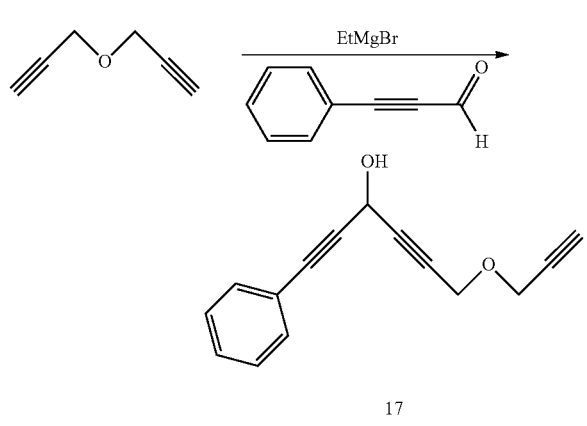

The preparation method of compound 17 is the same as that of compound 1, except the following characteristics:

the 1,6-heptadiyne used in embodiment 1 is replaced by propargyl ether with an equal molar amount. The 3-trimethylsilylpropynal in embodiment 1 is replaced by phenyl propargyl aldehyde

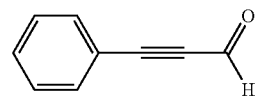

(synthesized according to literature *Org. Lett.* 2012, 14, 4906.) with an equal molar amount.

Yield of compound 17 is 70%. The yield of compound 17 is calculated as a molar amount of the compound 17 divided by a molar amount of propargyl ether×100%.

NMR data and high resolution mass spectrometry data of the compound 17 are as follows.

$^1$H NMR δ=7.43-7.45 (m, 2H), 7.29-7.33 (m, 3H), 5.20 (t, J=1.65 Hz, 1H), 4.33 (d, J=1.65 Hz, 2H), 4.26 (d, J=2.23 Hz 2H), 2.70 (br, 1H), 2.46 (t, J=2.23 Hz, 1H); $^{13}$C NMR δ=131.79, 128.72, 128.32, 122.01, 89.93, 88.26, 82.62, 78.85, 77.71, 75.42, 52.12, 56.72, 56.61; HRMS-ESI (m/z) calculated value $C_{15}H_{12}O_2Na$ [M+Na]$^+$ 247.0730, measured value 247.0726.

Embodiment 10

The present embodiment is to prepare the chain multiyne compound disclosed in the present invention.

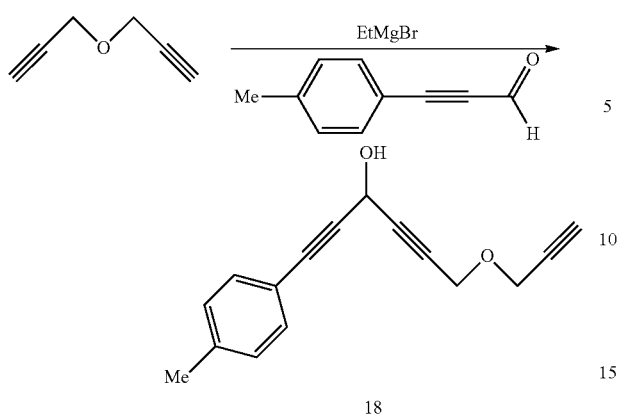

18

The preparation method of compound 18 is the same as that of compound 1, except the following characteristics:
the 1,6-heptadiyne used in embodiment 1 is replaced by propargyl ether with an equal molar amount. The 3-trimethylsilylpropynal in embodiment 1 is replaced by p-tolylpropynal

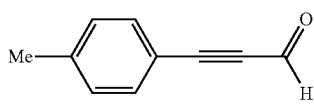

(synthesized according to literature Org. Lett. 2012, 14, 4906.) with an equal molar amount.

Yield of compound 18 is 62%. The yield of compound 18 is calculated as a molar amount of the compound 18 divided by a molar amount of propargyl ether×100%.

NMR data and high resolution mass spectrometry data of the compound 18 are as follows.

$^1$H NMR δ=7.42-7.44 (m, 2H), 7.26-7.30 (m, 2H), 5.21 (t, J=1.66 Hz, 1H), 4.30 (d, J=1.66 Hz, 2H), 4.27 (d, J=2.24 Hz 2H), 2.66 (br, 1H), 2.45 (t, J=2.24 Hz, 1H), 2.35 (s, 3H); $^{13}$C NMR δ=131.74, 128.70, 128.29, 122.11, 89.92, 88.29, 82.60, 78.83, 77.73, 75.45, 52.16, 56.73, 56.62, 27.45; HRMS-ESI (m/z) calculated value $C_{16}H_{14}O_2Na$ [M+Na]$^+$ 261.0886, measured value 261.0882.

Embodiment 11

The present embodiment is to prepare the chain multiyne compound disclosed in the present invention.

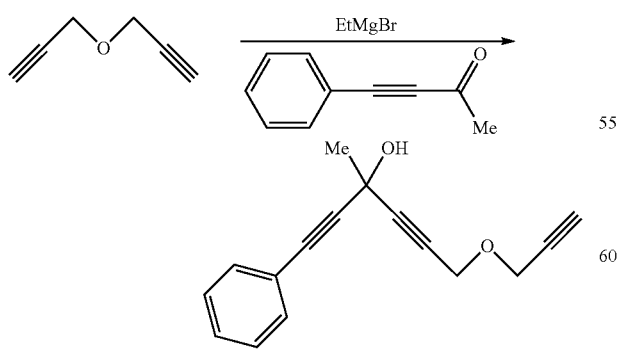

19

The preparation method of compound 19 is the same as that of compound 1, except the following characteristics:
the 1,6-heptadiyne used in embodiment 1 is replaced by propargyl ether with an equal molar amount. The 3-trimethylsilylpropynal in embodiment 1 is replaced by 4-phenyl-3-butyn-2-one

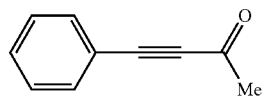

(purchased from Alfa Aesar (China) Chemical Co., Ltd., and a trademark number is MFCD0000877) with an equal molar amount.

Yield of compound 19 is 65%. The yield of compound 19 is calculated as a molar amount of the compound 19 divided by a molar amount of propargyl ether×100%.

NMR data and high resolution mass spectrometry data of the compound 19 are as follows.

$^1$H NMR δ=7.44-7.46 (m, 2H), 7.30-7.34 (m, 3H), 4.34 (s, 2H), 4.27 (d, J=2.22 Hz 2H), 2.59 (br, 1H), 2.46 (t, J=2.22 Hz, 1H), 1.87 (s, 3H); $^{13}$C NMR δ=131.81, 128.74, 128.31, 122.03, 89.94, 88.27, 82.61, 78.87, 77.70, 75.40, 60.23, 56.74, 56.62, 31.89; HRMS-ESI (m/z) calculated value $C_{16}H_{14}O_2Na$ [M+Na]$^+$ 261.0886, measured value 261.0879.

Embodiment 12

The present embodiment is to prepare the chain multiyne compound disclosed in the present invention.

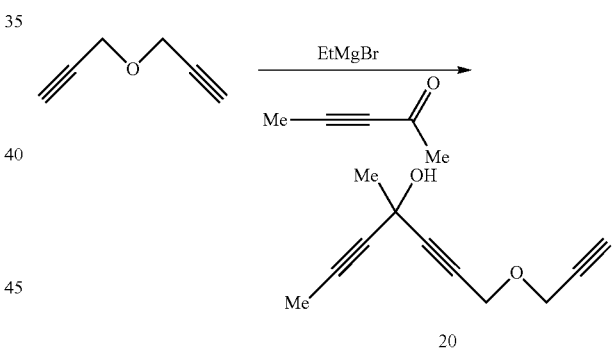

20

The preparation method of compound 20 is the same as that of compound 1, except the following characteristics:
the 1,6-heptadiyne used in embodiment 1 is replaced by propargyl ether with an equal molar amount. The 3-trimethylsilylpropynal in embodiment 1 is replaced by 3-pentyn-2-one

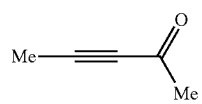

(synthesized according to J. Am. Chem. Soc. 2008, 130, 14713.) with an equal molar amount.

Yield of compound 20 is 60%. The yield of compound 20 is calculated as a molar amount of the compound 20 divided by a molar amount of propargyl ether×100%.

NMR data and high resolution mass spectrometry data of the compound 20 are as follows.

$^1$H NMR δ=4.35 (s, 2H), 4.29 (d, J=2.30 Hz 2H), 2.85 (br, 1H), 2.46 (t, J=2.30 Hz, 1H), 1.85 (s, 3H), 1.92 (s, 3H); $^{13}$C NMR δ=86.64, 85.27, 82.01, 78.57, 77.50, 75.20, 59.73, 56.62, 56.50, 31.59, 5.4; HRMS-ESI (m/z) calculated value $C_{11}H_{12}O_2Na$ [M+Na]$^+$ 199.0730, measured value 199.0727.

Embodiment 13

The present embodiment is to prepare the chain multiyne compound disclosed in the present invention.

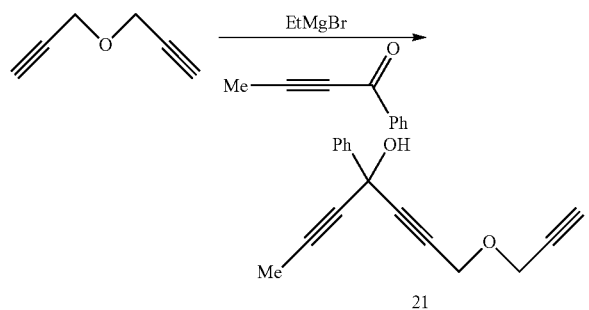

21

The preparation method of compound 21 is the same as that of compound 1, except the following characteristics:

the 1,6-heptadiyne used in embodiment 1 is replaced by propargyl ether with an equal molar amount. The 3-trimethylsilylpropynal in embodiment 1 is replaced by 1-phenyl-2-butyn-1-one

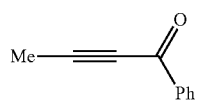 [SMILES: CC#CC(=O)c1ccccc1]

synthesized according to J. Am. Chem. Soc. 2008, 130, 14713.) with an equal molar amount.

Yield of compound 21 is 60%. The yield of compound 21 is calculated as a molar amount of the compound 21 divided by a molar amount of propargyl ether×100%.

NMR data and high resolution mass spectrometry data of the compound 21 are as follows.

$^1$H NMR δ=7.35-7.31 (m, 2H), 7.11-7.15 (m, 3H), 4.36 (s, 2H), 4.29 (d, J=2.28 Hz 2H), 2.85 (br, 1H), 2.48 (t, J=2.28 Hz, 1H), 1.93 (s, 3H); $^{13}$C NMR δ=131.20, 129.34, 127.11, 121.72, 86.82, 85.05, 82.11, 78.93, 77.81, 75.52, 65.71, 56.24, 56.12, 8.29; HRMS-ESI (m/z) calculated value $C_{16}H_{14}O_2Na$ [M+Na]$^+$ 261.0886, measured value 261.0878.

Embodiment 14

The present embodiment is to prepare the chain multiyne compound disclosed in the present invention.

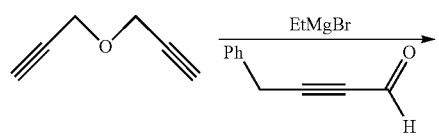

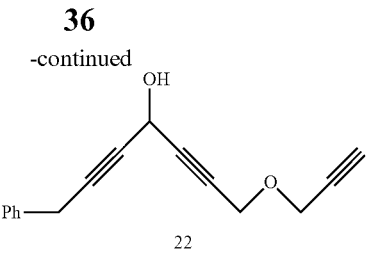

22

The preparation method of compound 22 is the same as that of compound 1, except the following characteristics:

the 1,6-heptadiyne used in embodiment 1 is replaced by propargyl ether with an equal molar amount. The 3-trimethylsilylpropynal in embodiment 1 is replaced by 4-phenyl-2-butyn-1-al

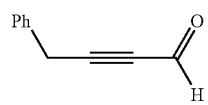 [SMILES: O=CC#CCc1ccccc1]

synthesized according to Angew. Chem., Int. Ed. 2014, 53, 4154.) with an equal molar amount.

Yield of compound 22 is 68%. The yield of compound 22 is calculated as a molar amount of the compound 22 divided by a molar amount of propargyl ether×100%.

NMR data and high resolution mass spectrometry data of the compound 22 are as follows.

$^1$H NMR δ=7.24-7.26 (m, 2H), 7.13-7.22 (m, 3H), 5.14 (br, 1H), 2.65 (br, 1H), 4.30 (d, J=1.57 Hz, 2H), 4.25 (d, J=2.27 Hz, 2H), 2.59 (d, J=2.25 Hz, 1H), 3.25 (d, J=1.60 Hz, 2H); $^{13}$C NMR δ=83.85, 80.75, 80.55, 80.13, 78.82, 75.47, 56.85, 56.746, 52.13; HRMS-ESI (m/z) calculated value $C_{16}H_{14}O_2Na$ [M+Na]$^+$ 261.0886, measured value 261.0878.

Embodiment 15

The present embodiment is to prepare the chain multiyne compound disclosed in the present invention.

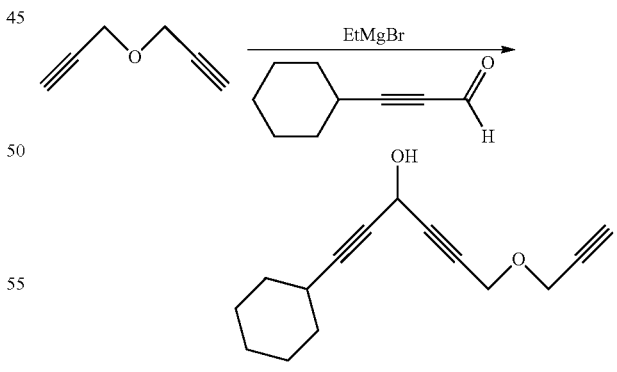

23

The preparation method of compound 23 is the same as that of compound 1, except the following characteristics:

the 1,6-heptadiyne used in embodiment 1 is replaced by propargyl ether with an equal molar amount. The 3-trimethylsilylpropynal in embodiment 1 is replaced by cyclohexyl propylaldehyde

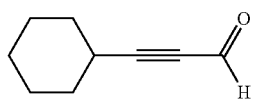

synthesized according to Angew. Chem., Int. Ed. 2014, 53, 4154.) with an equal molar amount.

Yield of compound 23 is 71%. The yield of compound 23 is calculated as a molar amount of the compound 23 divided by a molar amount of propargyl ether×100%.

NMR data and high resolution mass spectrometry data of the compound 23 are as follows.

$^1$H NMR δ=5.12 (t, J=1.53 Hz, 1H), 2.75 (br, 1H), 4.33 (d, J=1.53 Hz, 2H), 4.27 (d, J=2.23 Hz, 2H), 2.57 (d, J=2.23 Hz, 1H), 1.75 (m, 4H), 1.56 (m, 6H); $^{13}$C NMR δ=87.53, 83.85, 80.83, 80.63, 78.87, 75.67, 56.86, 56.75, 52.76, 33.52, 28.94, 25.63, 25.19; HRMS-ESI (m/z) calculated value $C_{15}H_{18}O_2Na$ [M+Na]$^+$ 253.1199, measured value 253.1198.

Embodiment 16

The present embodiment is to prepare the chain multiyne compound disclosed in the present invention.

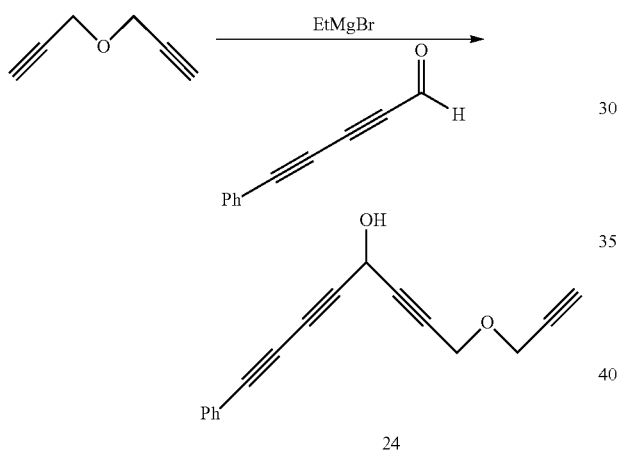

24

The preparation method of compound 24 is the same as that of compound 1, except the following characteristics:

the 1,6-heptadiyne used in embodiment 1 is replaced by propargyl ether with an equal molar amount. The 3-trimethylsilylpropynal in embodiment 1 is replaced by phenyl pentdialkylaldehyde

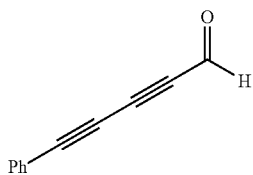

(synthesized according to J. Org. Chem. 2013, 78, 12018.) with an equal molar amount.

Yield of compound 24 is 54%. The yield of compound 24 is calculated as a molar amount of the compound 24 divided by a molar amount of propargyl ether×100%.

NMR data and high resolution mass spectrometry data of the compound 24 are as follows.

$^1$H NMR δ=7.30-7.48 (m, 5H), 5.17 (t, J=1.69 Hz, 1H), 4.32 (d, J=1.69 Hz, 2H), 4.28 (d, J=2.27 Hz, 2H), 2.60 (d, J=2.27 Hz, 1H), 2.53 (br, 1H); $^{13}$C NMR δ=132.48, 129.19, 128.35, 121.32, 81.23, 79.53, 77.64, 75.87, 73.54, 73.15, 72.56, 71.76, 56.85, 56.67, 52.86; HRMS-ESI (m/z) calculated value $C_{17}H_{12}O_2Na$ [M+Na]$^+$ 271.0730, measured value 271.0726.

Embodiment 17

The present embodiment is to prepare the chain multiyne compound disclosed in the present invention.

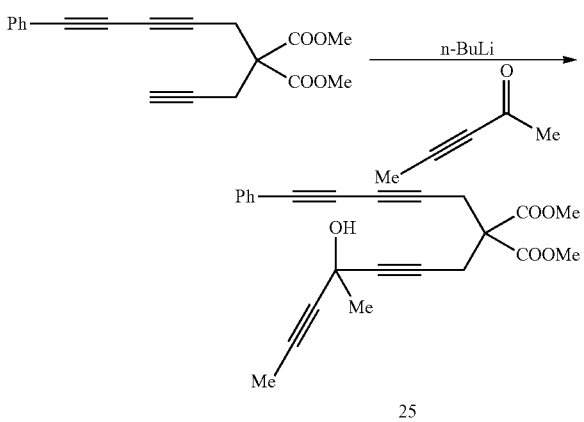

25

The preparation method of compound 25 is the same as that of compound 3, except the following characteristics:

the 2,2-dimethyl dipropargylmalonate used in step 1 of embodiment 2 is replaced by dimethyl 2-propargyl-2-(5-phenyl-2,4-pentadiynyl) malonate (synthesized according to literature J. Am. Chem. Soc. 2008, 130, 14713.) with an equal molar amount. The 3-trimethylsilylpropynal is replaced by 3-pentyn-2-one

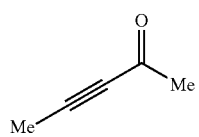

(synthesized according to literature J. Am. Chem. Soc. 2007, 129, 3826.) with an equal molar amount.

Yield of compound 25 is 50%. The yield of compound 25 is calculated as a molar amount of the compound 25 divided by a molar amount of 2,2-dimethyl dipropargylmalonate× 100%.

NMR data and high resolution mass spectrometry data of the compound 25 are as follows.

$^1$H NMR δ=7.30-7.48 (m, 5H), 3.77 (s, 6H), 3.15 (s, 2H), 3.09 (s, 2H), 2.65 (br, 1H), 1.75 (s, 3H), 1.80 (s, 3H); $^{13}$C NMR δ=168.87, 132.55, 129.16, 128.35, 121.42, 80.90, 79.31, 77.69, 75.87, 73.43, 72.24, 56.66, 53.35, 51.92, 31.58, 24.20, 23.31, 10.67; HRMS-ESI (m/z) calculated value $C_{24}H_{22}O_5Na$ [M+Na]$^+$ 413.1359, measured value 413.1358.

Embodiment 18

The present embodiment is to describe an application of the chain multiyne compound disclosed in the present invention in synthesizing the fused-ring metallacyclic compound.

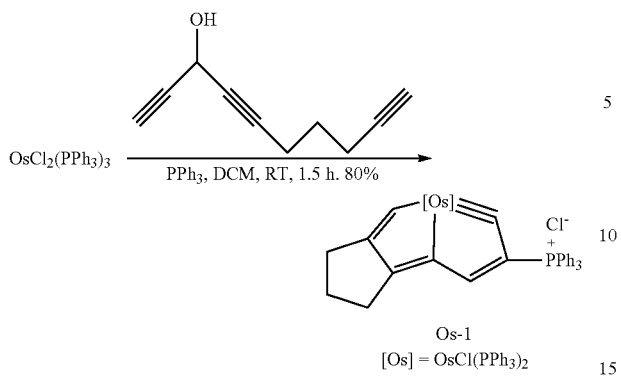

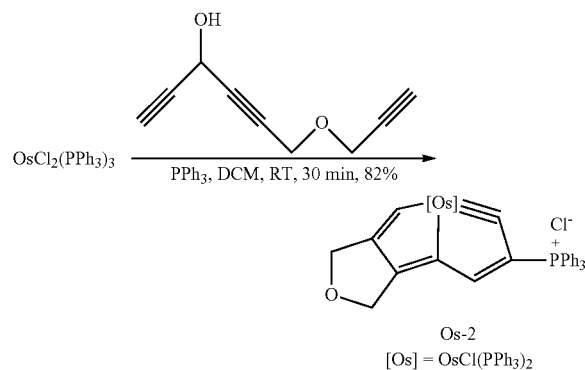

Wherein, DCM is dichloromethane. $OsCl_2(PPh_3)_3$ (500 mg, 0.48 mmol, synthesized according to literature *Inorg. Synth.*, 1989, 26, 184.) and $PPh_3$ (629 mg, 2.40 mmol, purchased from Sinopharm Chemical Reagent Co., Ltd., a trademark number is 80136926) were dissolved into 20 mL dichloromethane under an atmosphere of N2 and magnetic stirring.

A dichloromethane (dissolving 0.72 mmol HC≡CCH (OH)C≡C(CH$_2$)$_3$C≡CH into 2 mL dichloromethane solution) solution of HC≡CCH(OH)C≡(CH$_2$)C≡CH (105 mg, 0.72 mmol, the synthesis of this compound, refer to embodiment 1) was added gradually.

The solution reacted for 1.5 h at room temperature and a color of the solution was changed from green to red and a reaction mixture was obtained.

The obtained reaction mixture was concentrated under vacuum to 2 mL.

The concentrated mixture was washed with $Et_2O$ (diethyl ether) for 3 times, with 30 mL of diethyl ether at each time.

450 mg of red solid Os-1 was obtained, and yield is 80%. The yield of Os-1 is calculated as a molar amount of the Os-1 divided by a molar amount of $OsCl_2(PPh_3)_3 \times 100\%$.

NMR data and high resolution mass spectrometry data of the Os-1 are as follows.

$^1$H-NMR (300.1 MHz, CD$_2$Cl$_2$): δ=13.33 (s, 1H, C$^7$H), 7.61 (s, 1H, C$^3$H), 7.02-7.79 (m, 45H, Ph), 2.44. (dt, J(HH)=7.27 Hz, J(HH)=3.63 Hz, 2H, C$^{10}$H), 2.01 (tt, apparent quint, J(HH)=7.27 Hz, 2H, C$^9$H), 1.79 (t, J(HH)=7.27 Hz, 2H, C$^8$H); $^{31}$P{$^1$H} NMR (121.5 MHz, CD$_2$Cl$_2$): δ=5.76 (t, J(PP)=5.72 Hz, CPPh$_3$), 3.23 (d, J(PP)=5.72 Hz, OsPPh$_3$); $^{13}$C{$^1$H} NMR (75.5 MHz, CD$_2$Cl$_2$, plus $^{13}$C-dept 135, $^1$H-$^{13}$C HSQC and $^1$H-$^{13}$C HMBC): δ 321.56 (dt, apparent q, J(PC)=13.33 Hz, J(PC)=13.33 Hz, C$^1$), 216.58 (t, J(PC)=10.59 Hz, C$^7$), 180.44 (s, C$^5$), 175.50 (t, J(PC)=3.53 Hz, C$^6$), 172.04 (dt, J(PC)=23.30 Hz, J(PC)=3.21 Hz, C$^4$), 147.96 (dt, J(PC)=15.36 Hz, J(PC)=2.77 Hz, C$^3$), 128.00-135.48 (Ph), 125.89 (dt, J(PC)=95.84 Hz, J(PC)=3.61 Hz, C$^2$), 120.56 (d, J(PC)=90.83 Hz, Ph), 31.32 (s, C$^8$), 29.57 (s, C$^{10}$), 29.28 (s, C$^9$). HRMS (ESI): m/z calculated value [C$_{64}$H$_{53}$ClP3Os]$^+$, 1141.2658; measured value, 1141.2646.

Embodiment 19

The present embodiment is to describe an application of the chain multiyne compound disclosed in the present invention in synthesizing the fused-ring metallacyclic compound (osmapentalyne Os-2).

A preparation method of Os-2 is the same as that of Os-1 of embodiment 18, except the following characteristics:

the HC≡CCH(OH)C≡C(CH$_2$)$_3$C≡CH used in embodiment 18 is replaced by HC≡CCH(OH)C≡CCH$_2$OCH$_2$C≡CH (the preparation method of this compound refers to embodiment 3) with an equal molar amount.

Red solid Os-2 is obtained, and its yield is 82%. The yield of Os-2 is calculated as a molar amount of the Os-2 divided by a molar amount of $OsCl_2(PPh_3)_3 \times 100\%$.

NMR data and high resolution mass spectrometry data of the Os-2 are as follows.

$^1$H-NMR (300.1 MHz, CD$_2$Cl$_2$): δ=13.27 (s, 1H, C$^7$H), 7.69 (s, 1H, C$^3$H), 7.01-7.79 (Ph 46H, Ph and above-mentioned C$^3$H), 4.55 (s, C$^9$H), 3.89 (s, C$^8$H); $^{31}$P{$^1$H} NMR (121.5 MHz, CD$_2$Cl$_2$): δ=6.05 (t, J(PP)=4.67 Hz, CPPh$_3$), 2.49 (d, J(PP)=4.67 Hz, OsPPh$_3$); $^{13}$C{$^1$H} NMR (75.5 MHz, CD$_2$Cl$_2$, plus $^{13}$C-dept 135, $^1$H-$^{13}$C HSQC and $^1$H-$^{13}$C HMBC): δ 302.51 (dt, apparent q, J(PC)=13.54 Hz, J(PC)=13.54 Hz, C$^1$), 211.53 (t, J(PC)=11.06 Hz, C$^7$), 172.79 (s, C$^5$), 171.55 (t, J(PC)=4.96 Hz, C$^6$), 169.26 (dt, J(PC)=23.95 Hz, J(PC)=2.97 Hz, C$^4$), 150.34 (d, J(PC)=15.37 Hz, C$^3$), 120.27-135.82 (Ph), 119.81 (d, J(PC)=90.43 Hz, C$^2$), 71.39 (s, C$^8$), 69.17 (s, C$^9$); HRMS (ESI): m/z calculated value [C$_{63}$H$_{51}$ClOP$_3$Os]$^+$, 1143.2451; measured value, 1143.2435.

Embodiment 20

The present embodiment is to describe an application of the chain multiyne compound disclosed in the present invention in synthesizing the fused-ring metallacyclic compound (osmapentalyne Os-3).

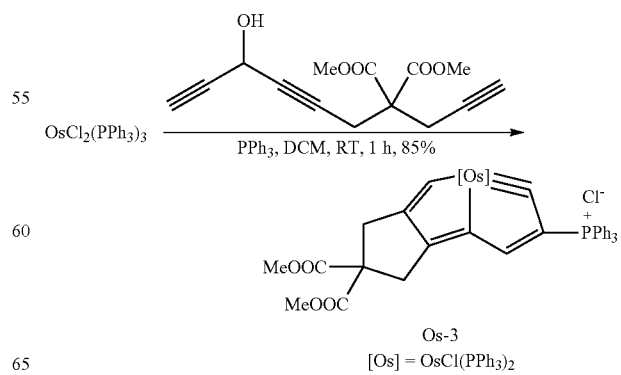

A preparation method of Os-3 is the same as that of Os-1 of embodiment 18, except the following characteristics:

the HC≡CCH(OH)C≡C(CH$_2$)$_3$C≡CH used in embodiment 18 is replaced by HC≡CCH(OH)C≡CCH$_2$C(COOMe)$_2$CH$_2$C≡CH (the preparation method of this compound refers to embodiment 2) with an equal molar amount.

Red solid Os-3 is obtained, and its yield is 85%. The yield of Os-3 is calculated as a molar amount of the Os-3 divided by a molar amount of OsCl$_2$(PPh$_3$)$_3$×100%.

NMR data and high resolution mass spectrometry data of the Os-3 are as follows.

$^1$H-NMR (500.2 MHz, CD$_2$Cl$_2$): δ=13.16 (s, 1H, C$^7$H), 7.67 (s, 1H, C$^3$H), 7.02-7.80 (m, 46H, Ph and above-mentioned C$^3$H), 3.64 (s, 6H, COOCH$_3$), 3.12 (s, C$^{10}$H), 2.44 (s, C$^8$H); $^{31}$P{$^1$H} NMR (202.5 MHz, CD$_2$Cl$_2$): δ=5.79 (t, J(P,P)=5.00 Hz, CPPh$_3$), 3.31 (d, J(P,P)=5.00 Hz, OsPPh$_3$); $^{13}$C{$^1$H} NMR (125.8 MHz, CD$_2$Cl$_2$, plus $^{13}$C-dept 135, $^1$H-$^{13}$C HSQC and $^1$H-$^{13}$C HMBC): δ 321.57 (dt, apparent q, J(PC)=13.33 Hz, J(PC)=13.33 Hz, C$^1$), 217.23 (q, J(P,C)=9.78 Hz, J(P,C)=19.55 Hz, C$^7$), 173.07 (s, C$^5$), 172.16 (s, COOCH$_3$), 171.81 (d, J(P,C)=23.02 Hz, C$^4$), 170.12 (s, C$^6$), 149.22 (d, J(P,C)=16.31 Hz, C$^3$), 128.18-135.61 (Ph), 128.15 (dt, J(P,C)=81.30 Hz, J(PC)=3.64 Hz, C$^2$), 120.30 (d, J(PC)=91.07 Hz, Ph), 64.38 (s, C$^9$), 53.54 (s, COOCH$_3$), 39.07 (s, C$^8$), 37.62 (s, C$^{10}$); HRMS (ESI): m/z calculated value [C$_{68}$H$_{57}$ClO$_4$P$_3$Os]$^+$, 1257.2768; measured value, 1257.2771.

Embodiment 21

The present embodiment is to describe an application of the chain multiyne compound disclosed in the present invention in synthesizing the fused-ring metallacyclic compound (ru-pentalyne Ru-1).

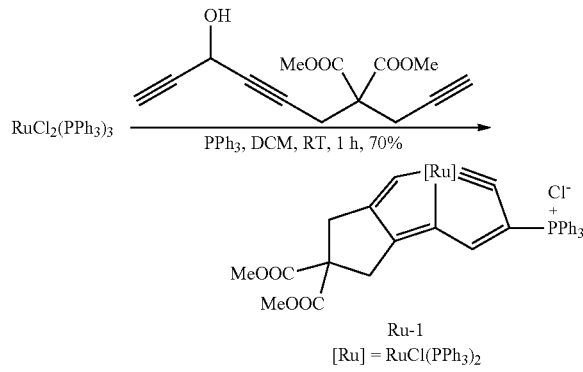

Ru-1
[Ru] = RuCl(PPh$_3$)$_2$

A preparation method of Ru-1 is the same as that of Os-1 of embodiment 18, except the following characteristics:

the HC≡CCH(OH)C≡C(CH$_2$)$_3$C≡CH used in embodiment 18 is replaced by HC≡CCH(OH)C≡CCH$_2$C(COOMe)$_2$CH$_2$C≡CH (the preparation method of this compound refers to embodiment 2) with an equal molar amount.

Red solid Ru-1 is obtained, and its yield is 70%. The yield of Ru-1 is calculated as a molar amount of the Ru-1 divided by a molar amount of RuCl$_2$(PPh$_3$)$_3$×100%.

NMR data and high resolution mass spectrometry data of the Ru-1 are as follows.

$^1$H NMR (300.1 MHz, CD$_2$Cl$_2$): δ=13.06 (s, 1H, C$^7$H), 7.33 (1H, C$^3$H, obtained by HSQC), 6.99-7.81 (46H, Ph and above-mentioned C$^3$H), 3.64 (s, 6H, COOCH$_3$), 2.96 (t, J(H,H)=3.63, C$^{10}$H), 2.76 (s, C$^8$H); $^{31}$P{$^1$H} NMR (121.5 MHz, CD$_2$Cl$_2$): δ=29.59 (d, J(P,P)=5.89 Hz, RuPPh$_3$), 6.38 (t, J(P,P)=5.89 Hz, CPPh$_3$); $^{13}$C{$^1$H} NMR (75.5 MHz, CD$_2$Cl$_2$, plus $^{13}$C-dept 135, $^1$H-$^{13}$C HSQC and $^1$H-$^{13}$C HMBC): δ=356.95 (br, C$^1$), 251.89 (t, J(P,C)=11.96, C$^7$), 190.23 (dt, J(P,C)=25.65 Hz, J(P,C)=4.90 Hz, C$^4$), 180.98 (d, J(P,C)=1.97 Hz, C$^5$), 171.77 (s, COOCH$_3$), 164.57 (t, J(P,C)=4.24 Hz, C$^6$), 154.99 (dt, J(P,C)=14.44 Hz, J(P,C)=3.07 Hz, C$^3$), 128.18-135.76 (other aromatic carbons), 122.86 (dt, J(P,C)=92.99 Hz, J(P,C)=4.02 Hz, C$^2$), 119.57 (other aromatic carbons), 64.14 (s, C$^9$), 53.63 (s, COOCH$_3$, obtained by $^{13}$C-dept 135), 39.06 (s, C$^8$), 37.35 (s, C$^{10}$); HRMS (ESI): m/z calculated value [C$_{68}$H$_{57}$ClO$_4$P$_3$Ru]$^+$, 1167.2212; measured value, 1167.2215.

Embodiment 22

The present embodiment is to describe an application of the chain multiyne compound disclosed in the present invention in synthesizing the fused-ring metallacyclic compound (rhodium double five-membered ring compound Rh-1).

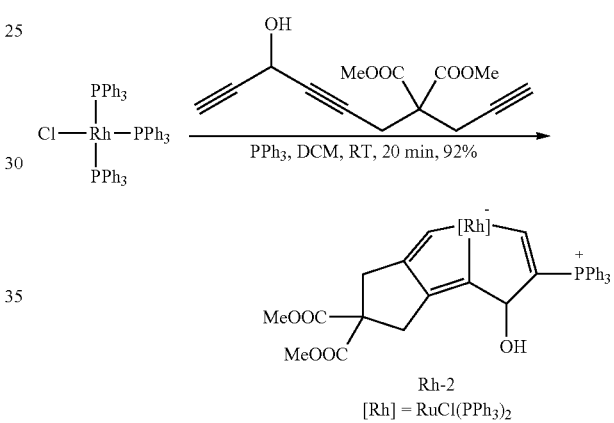

Rh-2
[Rh] = RuCl(PPh$_3$)$_2$

A preparation method of Ru-2 is the same as that of Os-1 of embodiment 18, except the following characteristics:

the HC≡CCH(OH)C≡C(CH$_2$)$_3$C≡CH used in embodiment 18 is replaced by HC≡CCH(OH)C≡CCH$_2$C(COOMe)$_2$CH$_2$C≡CH (the preparation method of this compound refers to embodiment 2) with an equal molar amount. The OsCl$_2$(PPh$_3$)$_3$ is simultaneously replaced by RhCl(PPh$_3$)$_3$.

Yellow solid Ru-2 is obtained, and its yield is 91%. The yield of Ru-2 is calculated as a molar amount of the Ru-2 divided by a molar amount of RhCl(PPh$_3$)$_3$×100%.

NMR data and high resolution mass spectrometry data of the Ru-2 are as follows.

$^1$H-NMR (600.1 MHz, CD$_2$Cl$_2$): δ=10.27 (d, J(PH)=29.75 Hz, 1H, C$^1$H), 6.87-8.20 (45H, Ph), 6.53 (s, 1H, C$^7$H), 3.57 (s, 3H, COOCH$_3$), 3.54 (s, 3H, COOCH$_3$), 3.45 (d, J(HH)=8.95 Hz, 1H, C$^3$H), 2.35 (d, J(HH)=16.47 Hz, 1H, C$^{10}$H), 2.27 (d, J(HH)=16.47 Hz, 1H, C$^{10}$H), 2.01 (d, J(HH)=17.02 Hz, 1H, C$^8$H), 1.78 (d, J(HH)=17.02 Hz, 1H, C$^8$H), 0.17 (d, J(HH)=8.95 Hz, 1H, OH); $^{31}$P{$^1$H} NMR (242.9 MHz, CD$_2$Cl$_2$): δ=33.33 (ddd, J(PP)=431.55 Hz, J(RhP)=126.88 Hz, J(PP)=5.74 Hz, RhPPh$_3$), δ=31.04 (ddd, J(PP)=431.55 Hz, J(RhP)=126.88 Hz, J(PP)=5.74 Hz, RhPPh$_3$), 8.00 (br, CPPh$_3$); $^{13}$C{$^1$H} NMR (150.5 MHz, CD$_2$Cl$_2$, plus $^{13}$C-dept 135, $^1$H-$^{13}$C HSQC and $^1$H-$^{13}$C HMBC): δ=221.27 (br, C$^1$), 174.08 (s, COOCH$_3$), 173.27 (s, COOCH$_3$), 167.45 (br, C$^4$), 154.85 (s, C$^6$), 153.49 (br, C$^7$), 145.57 (s, C$^5$), 127.32-136.42 (Ph), 122.91 (d, J(PC)=46.59 Hz, C$^2$), 122.89 (d, J(PC)=84.89 Hz, Ph), 80.32 (d, J(PC)=25.69 Hz, C$^3$), 64.39 (s, C$^9$), 52.90 (s, COOCH$_3$), 52.70 (s, COOCH$_3$), 39.06 (s, C$^{10}$), 36.01 (s, C$^{10}$); HRMS (ESI): m/z calculated value [C$_{68}$H$_{60}$ClO$_5$P$_3$Rh]$^+$, 1187.2392 [M+H]$^+$; measured value, 1187.2418.

Embodiment 23

The present embodiment is to describe an application of the chain multiyne compound disclosed in the present invention in synthesizing the fused-ring metallacyclic compound (Ir-pentalene Ir-1).

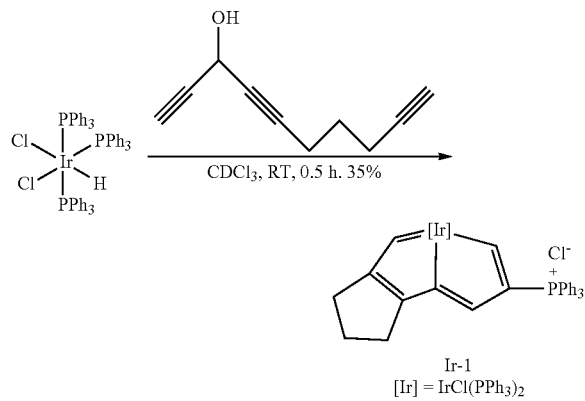

A preparation method of Ir-1 is the same as that of Os-1 of embodiment 18, except the following characteristics:

the OsCl$_2$(PPh$_3$)$_3$ used in embodiment 18 is replaced by IrHCl$_2$(PPh$_3$)$_3$ (the preparation method of this compound refers to embodiment 1).

Yield of Ir-1 is 35%. The yield of Ru-2 is calculated as a molar amount of the Ir-1 divided by a molar amount of IrHCl$_2$(PPh$_3$)$_3$×100%.

NMR data and high resolution mass spectrometry data of the Ir-1 are as follows.

$^1$H-NMR (600.1 MHz, CDCl$_3$): δ=14.34 (s, 1H, C$^7$H), 12.66 (d, J(PH)=20.03 Hz, 1H, C$^1$H), 8.67 (t, J(PH)=2.35 Hz, 1H, C$^3$H), 6.98-7.90 (m, 45H, Ph), 2.56 (m, 2H, C$^{10}$H), 1.64 (tt, apparent quint, J(HH)=7.44 Hz, 2H, C$^9$H), 1.15 (t, J(HH)=7.44 Hz, 2H, C$^8$H); $^{31}$P{$^1$H} NMR (242.9 MHz, CDCl$_3$): δ=10.91 (t, J(PP)=5.97 Hz, CPPh$_3$), -5.77 (d, J(PP)=5.97 Hz, IrPPh$_3$); $^{13}$C{$^1$H} NMR (150.9 MHz, CDCl$_3$, plus $^{13}$C-dept 135, $^1$H-$^{13}$C HSQC and $^1$H-$^{13}$C HMBC): δ=230.16 (br, C$^7$), 215.13 (br, C$^1$), 186.44 (s, C$^5$), 184.96 (s, C$^6$), 169.34 (dt, J(PC)=22.59 Hz, J(PC)=2.90 Hz, C$^4$), 151.98 (d, J(PC)=24.44 Hz, C$^3$), 137.51 (dt, J(PC)=62.94 Hz, J(PC)=3.21 Hz, C$^2$), 119.36-135.16 (Ph), 31.75 (s, C$^8$), 31.00 (s, C$^{10}$), 28.75 (s, C$^9$); HRMS (ESI): m/z calculated value [C$_{64}$H$_{54}$ClP$_3$Ir]$^+$, 143.2748; measured value, 1143.2739.

Embodiment 24

The present embodiment is to describe an application of the chain multiyne compound disclosed in the present invention in synthesizing the fused-ring metallacyclic compound (osmapentalene Os-4).

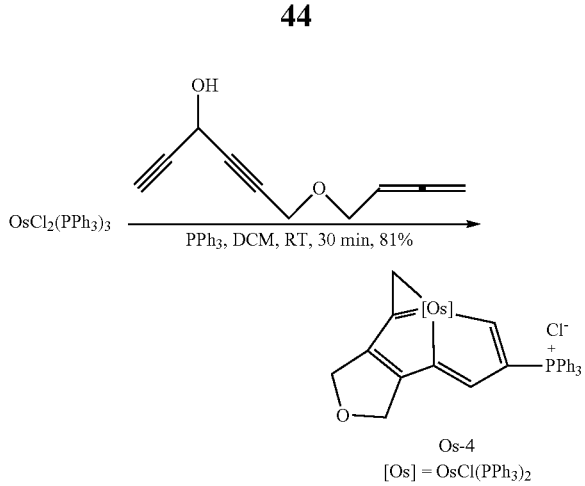

A preparation method of Os-4 is the same as that of Os-1 of embodiment 18, except the following characteristics:

the HC≡CCH(OH)C≡C(CH$_2$)$_3$C≡CH used in embodiment 18 is replaced by HC≡CCH(OH)C≡CCH$_2$OCH$_2$CH=C=CH (the preparation method of this compound refers to embodiment 7) with an equal molar amount.

Red solid Os-4 is obtained. Yield of Os-4 is 80%. The yield of Os-4 is calculated as a molar amount of the Os-4 divided by a molar amount of OsCl$_2$(PPh$_3$)$_3$×100%.

NMR data and high resolution mass spectrometry data of the Os-4 are as follows.

$^1$H-NMR (500.2 MHz, CD$_2$Cl$_2$): δ=14.01 (d, J(P,H)=17.17 Hz, 1H, C$^1$H), 8.21 (s, 1H, C$^3$H), 6.90-7.81 (m, 45H, Ph), 4.12 (s, 2H, C$^9$H), 3.21 (s, 2H, C$^{10}$H), 3.03 (s, 2H, C$^8$H); $^{31}$P{$^1$H} NMR (202.5 MHz, CD$_2$Cl$_2$): δ=11.81 (d, J(P,P)=4.95 Hz, CPPh$_3$), -13.19 (d, J(PP)=4.95 Hz, OsPPh$_3$); $^{13}$C{$^1$H} NMR (125.8 MHz, CD$_2$Cl$_2$, plus $^{13}$C-dept 135, $^1$H-$^{13}$C HSQC and $^1$H-$^{13}$C HMBC): δ=339.19 (br, C$^1$), 226.16 (t, J(P,C)=4.37 Hz, C$^7$), 183.46 (s, C$^5$), 176.00 (d, J(PC)=25.20 Hz, C$^4$), 163.13 (s, C$^6$), 145.12 (d, J(P,C)=21.87 Hz, C$^3$), 134.66 (dt, J(P,C)=70.73 Hz, J(P,C)=3.92 Hz, C$^2$), 118.46-134.17 (Ph), 69.92 (s, C$^{10}$), 65.41 (s, C$^9$), 23.08 (s, C$^8$); HRMS (ESI): m/z calculated value [C$_{64}$H$_{53}$ClOP$_3$Os]$^+$, 1157.2607; measured value, 1157.2594.

Embodiment 25

The present embodiment is to describe an application of the chain multiyne compound disclosed in the present invention in synthesizing the fused-ring metallacyclic compound (osmapentalene Os-5).

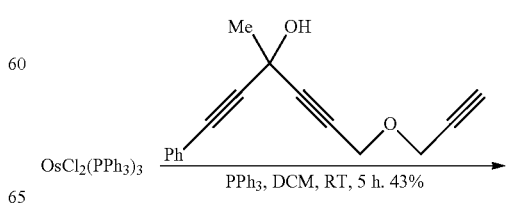

-continued

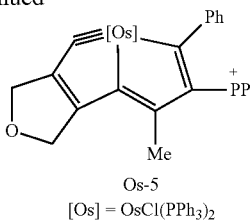

Os-5
[Os] = OsCl(PPh$_3$)$_2$

A preparation method of Os-5 is the same as that of Os-1 of embodiment 18, except the following characteristics:

the HC≡CCH(OH)C≡C(CH$_2$)$_3$C≡CH used in embodiment 18 is replaced by PhC≡CCMe(OH)C≡CCH$_2$OCH$_2$C≡CH (the preparation method of this compound is the same as compound 5) with an equal molar amount.

Red solid Os-5 is obtained. Yield of Os-5 is 43%. The yield of Os-5 is calculated as a molar amount of the Os-5 divided by a molar amount of OsCl$_2$(PPh$_3$)$_3$×100%.

NMR data and high resolution mass spectrometry data of the Os-5 are as follows.

$^1$H-NMR (300.1 MHz, CD$_2$Cl$_2$): δ=7.05-7.72 (m, 50H, Ph), 4.45 (s, C$^1$H), 3.78 (s, C$^8$H), 2.25 (s, CH$_3$); $^{31}$P{$^1$H} NMR (121.5 MHz, CD$_2$Cl$_2$): δ=14.01 (t, J(PP)=4.72 Hz, CPPh$_3$), 6.86 (d, J(PP)=4.72 Hz, OsPPh$_3$); $^{13}$C{$^1$H} NMR (75.5 MHz, CD$_2$Cl$_2$, plus $^{13}$C-dept 135, $^1$H-$^{13}$C HSQC and $^1$H-$^{13}$C HMBC): δ 330.11 (br, C$^7$), 225.2 (br, C$^1$), 171.79 (s, C$^5$), 171.34 (t, J(PC)=4.94 Hz, C$^6$), 168.11 (dt, J(PC)=23.45 Hz, J(PC)=2.85 Hz, C$^4$), 148.33 (d, J(PC)=15.37 Hz, C$^3$), 120.25-135.76 (Ph), 118.11 (d, J(PC)=90.21 Hz, C$^2$), 71.35 (s, C$^8$), 69.05 (s, C$^9$), 25.12 (s, CH$_3$); HRMS (ESI): m/z calculated value [C$_{70}$H$_{57}$ClOP$_3$Os]$^+$, 1233.2920; measured value, 1233.2917.

The preferred embodiments of the present invention are described in detail above. However, the present invention is not limited to the specific details of the above embodiments. Various simple modifications made to the technical solutions of the present invention within the scope of the technical concept of the present invention all belong to the protection scope of the present invention.

Additionally, any combination of various embodiments of the present invention may also be performed as long as it does not violate the spirit of the present invention, and should also be regarded as a disclosure of the present invention.

What is claimed is:
1. A chain multiyne compound of Formula I:

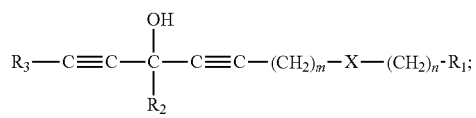

Formula I wherein, X is any one of —O—, —S—, —CH$_2$—, —C(CH$_3$)$_2$—, —CHCH$_3$—, —C(COOMe)$_2$-, —C(COOEt)$_2$-, —C(COCH$_3$)(COOMe)-, —C(Cy)(COOMe)-, —C(CH$_2$CH$_2$Br)$_2$—, —C(CN)$_2$—, —C(NO$_2$)$_2$—, —SiH$_2$—, —SiMe$_2$-, —SiPh$_2$-, —NH—,

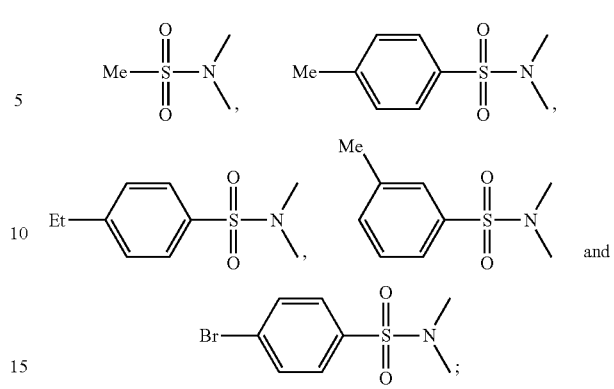

R$_1$ is any one of nitrile group, acetenyl,

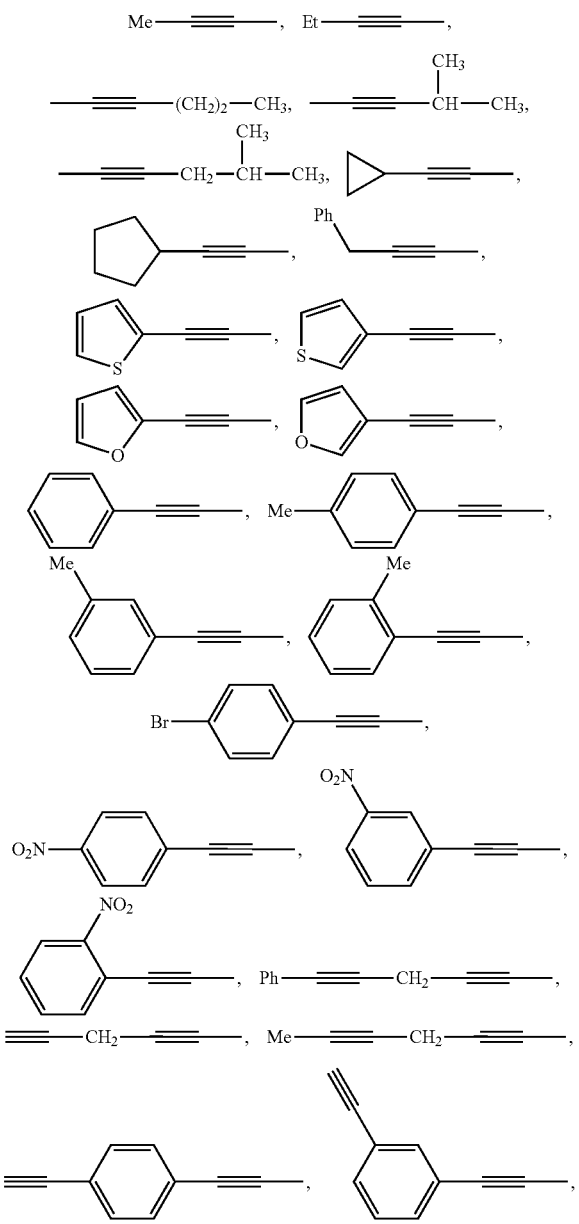

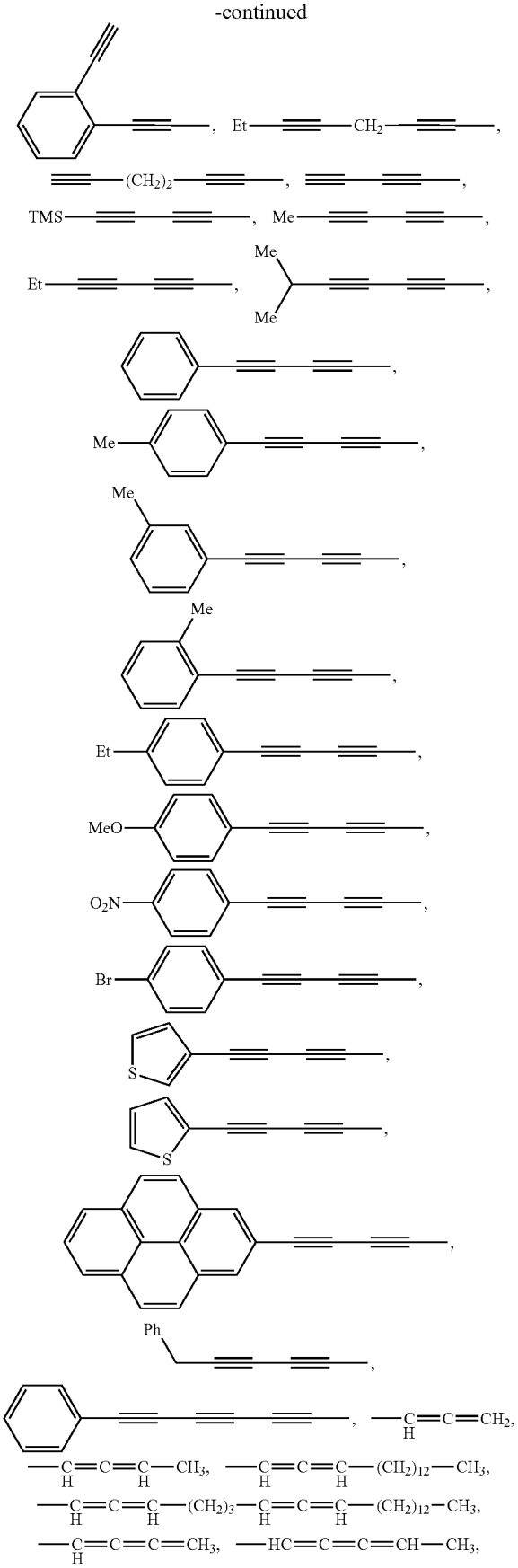
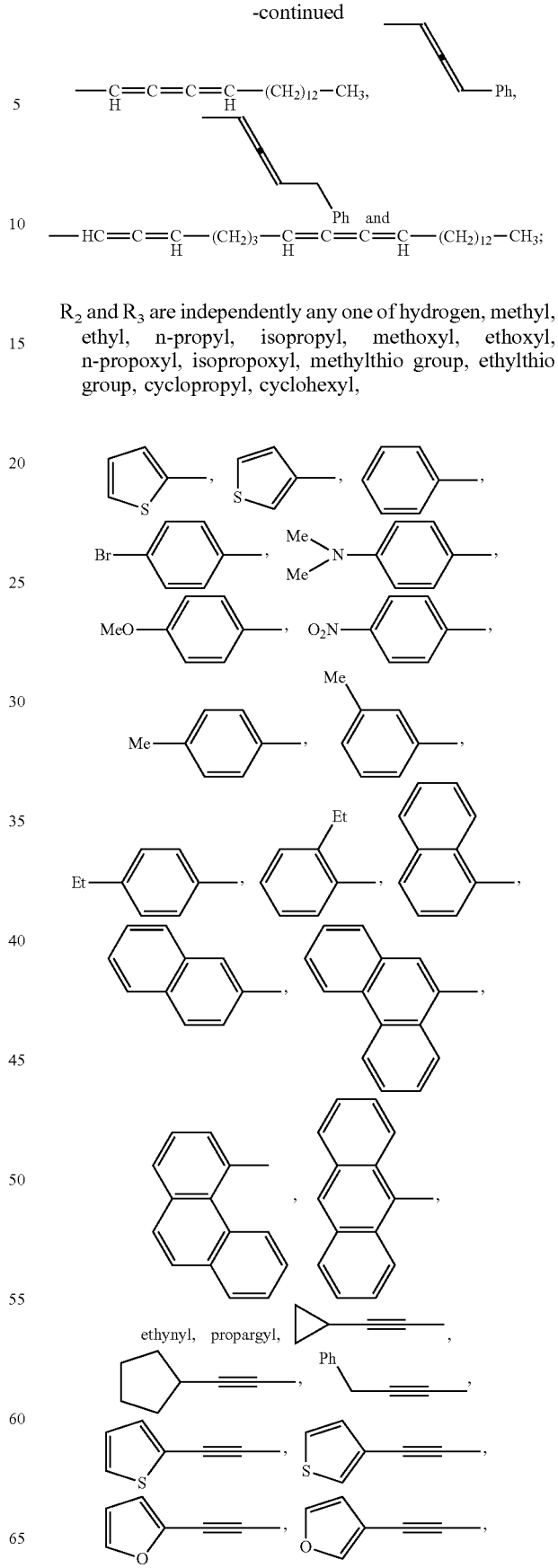
$R_2$ and $R_3$ are independently any one of hydrogen, methyl, ethyl, n-propyl, isopropyl, methoxyl, ethoxyl, n-propoxyl, isopropoxyl, methylthio group, ethylthio group, cyclopropyl, cyclohexyl,

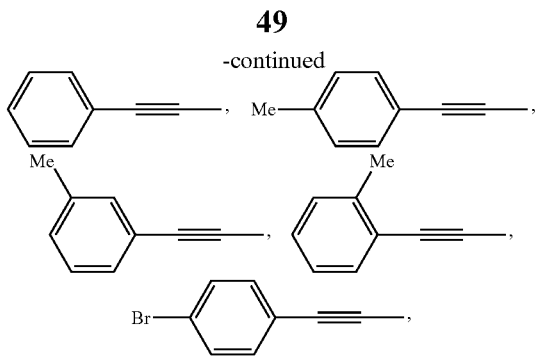

benzyl and phenethyl;
wherein m and n are independently integers from 1-6, and m+n<8.

2. A chain multiyne compound of Formula I:

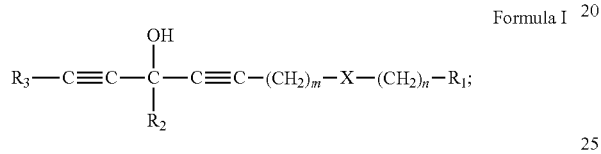

wherein X is any one of —O—, —S—, —CR$_4$R$_5$—, —SiR$_6$R$_7$— and —NR$_8$—, R$_4$, R$_5$, R$_6$, R$_7$ and R$_8$ are independently any one of hydrogen, C$_1$-C$_{20}$ alkyl, C$_1$-C$_{20}$ ester group, C$_1$-C$_{20}$ acyl, C$_3$-C$_{20}$ cycloalkyl, C$_1$-C$_{20}$ alkyl halide, nitrile group, nitryl, substituted or unsubstituted aryl and

R$_9$ is any one of C$_1$-C$_8$ alkyl and substituted or unsubstituted phenyl;

R$_1$ is any one of nitrile group, substituted or unsubstituted C$_2$-C$_{30}$ alkynyl, substituted or unsubstituted C$_4$-C$_{30}$ multiyne, substituted or unsubstituted C$_3$-C$_{30}$ cumulene group, without containing a structure unit of —C≡CCH(OH)C≡C—;

R$_2$ and R$_3$ are independently any one of hydrogen, substituted or unsubstituted aryl, substituted or unsubstituted C$_1$-C$_8$ alkyl, substituted or unsubstituted C$_1$-C$_8$ alkoxy, substituted or unsubstituted C$_1$-C$_8$ alkylthiol, substituted or unsubstituted C$_3$-C$_8$ cycloalkyl and substituted or unsubstituted C$_2$-C$_8$ alkynyl, without containing a structure unit of —C≡CCH(OH)C≡C—; and m and n are independently integers from 1-6, and m+n<8; wherein the multiyne compound is any one of the following compounds:

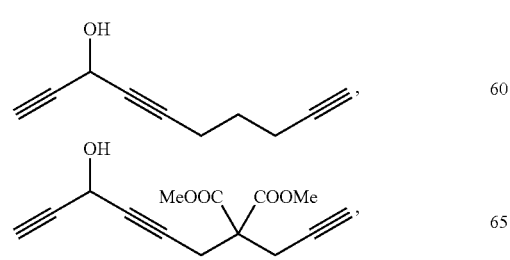

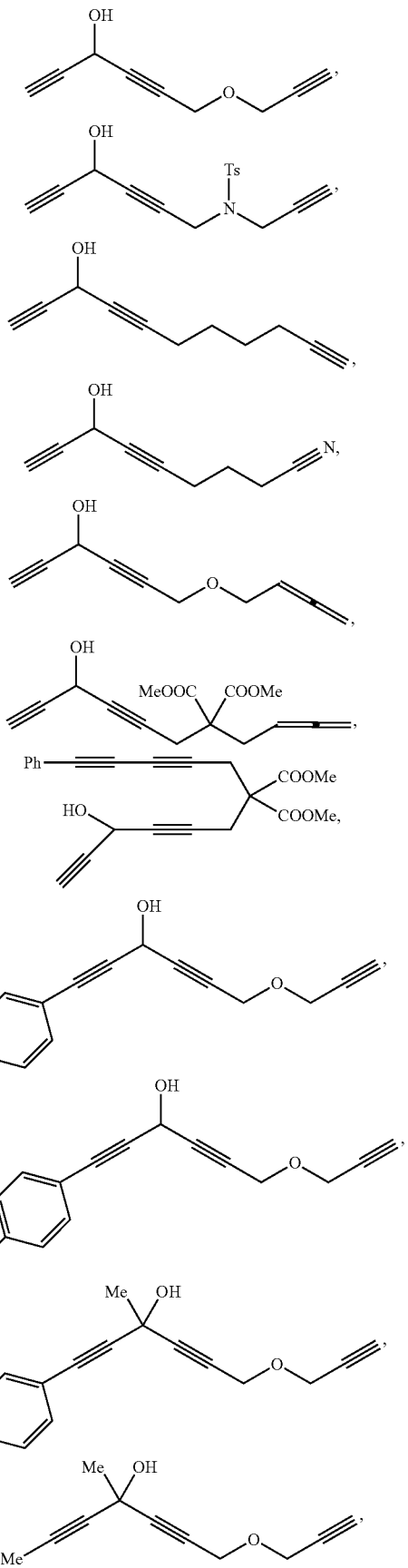

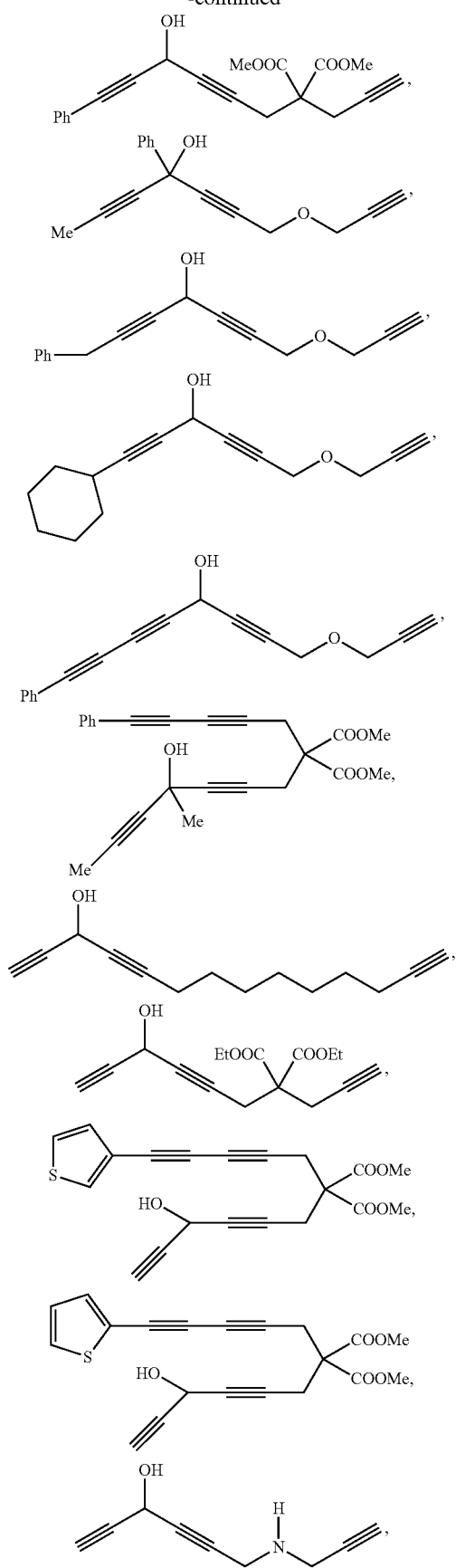
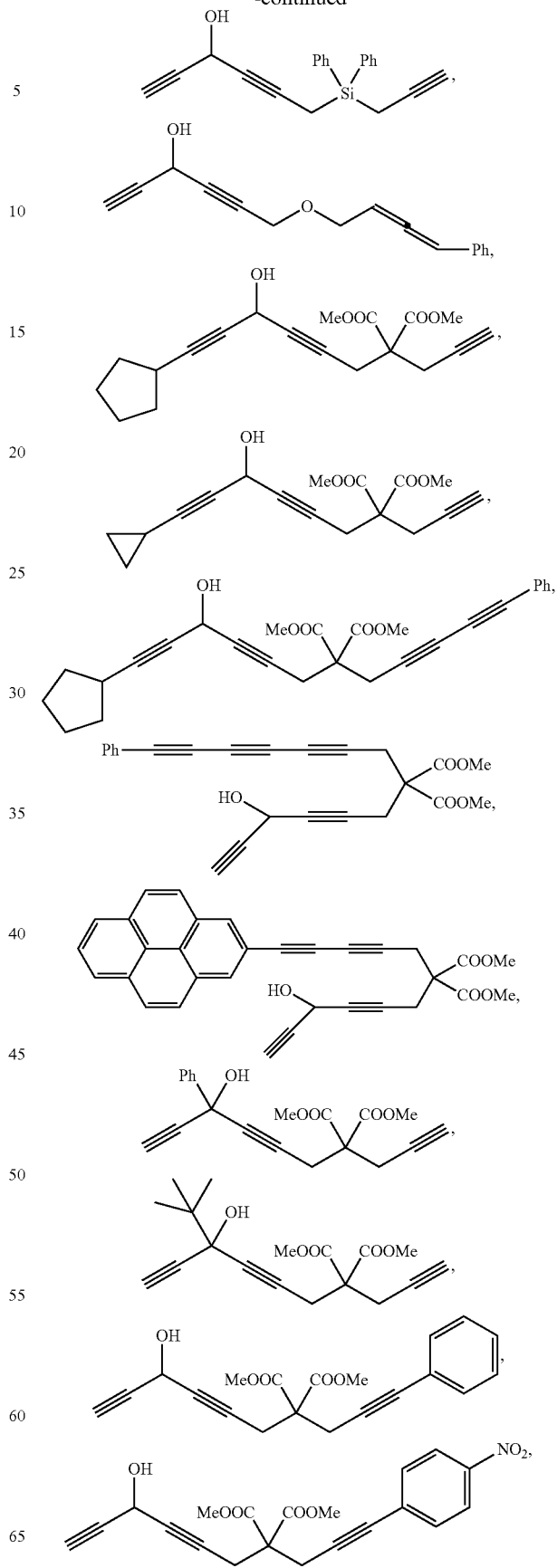

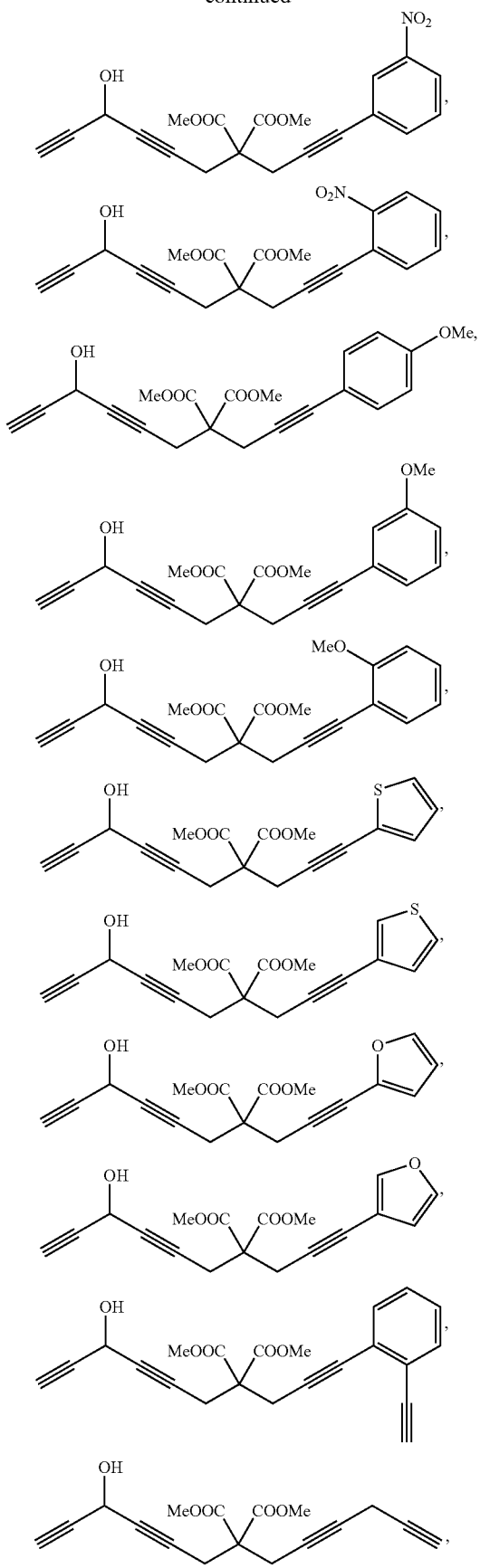

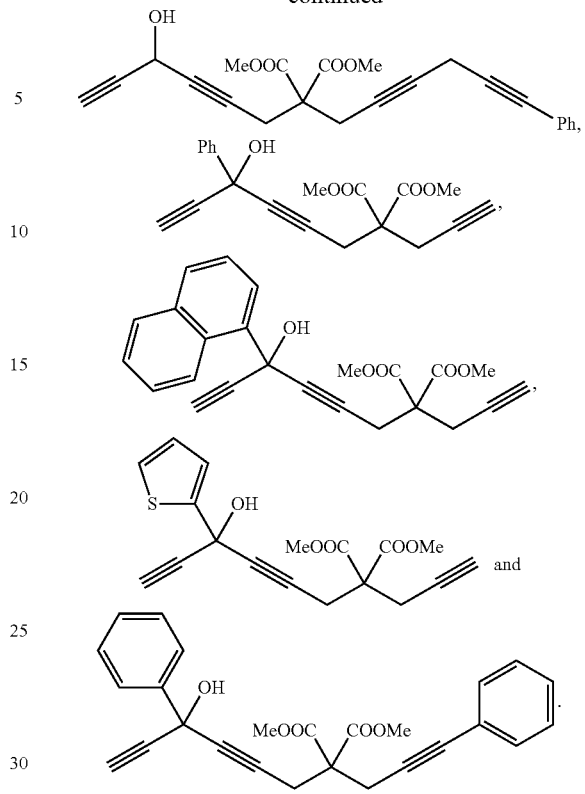

3. A method of synthesizing a fused-ring metallacyclic compound, comprising reacting the chain multiyne compound of Formula I with a metal complex Formula I

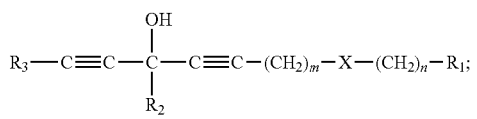

wherein X is any one of —O—, —S—, —CR$_4$R$_5$—, —SiR$_6$R$_7$— and —NR$_8$—; R$_4$, R$_5$, R$_6$, R$_7$ and R$_8$ are independently any one of hydrogen, C$_1$-C$_{20}$ alkyl, C$_1$-C$_{20}$ ester group, C$_1$-C$_{20}$ acyl, C$_3$-C$_{20}$ cycloalkyl, C$_1$-C$_{20}$ alkyl halide, nitrile group, nitryl, substituted or unsubstituted aryl and

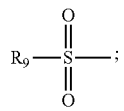

R$_9$ is any one of C$_1$-C$_8$ alkyl and substituted or unsubstituted phenyl;

R$_1$ is any one of nitrile group, substituted or unsubstituted C$_2$-C$_{30}$ alkynyl, substituted or unsubstituted C$_4$-C$_3$o multiyne, substituted or unsubstituted C$_3$-C$_{30}$ cumulene group, without containing a structure unit of —C≡CCH(OH)C≡C—;

R$_2$ and R$_3$ are independently any one of hydrogen, substituted or unsubstituted aryl, substituted or unsubstituted $C_1$-$C_8$ alkyl, substituted or unsubstituted $C_1$-$C_8$ alkoxy, substituted or unsubstituted $C_1$-$C_8$ alkylthiol, substituted or unsubstituted $C_3$-$C_8$ cycloalkyl and substituted or unsubstituted $C_2$-$C_8$ alkynyl, without containing a structure unit of —C≡CCH(OH)C≡C—; and m and n are independently integers from 1-6, and m+n<8; wherein the metal complex is $DE_aL_b$;

D is any one of Fe, Co, Ni, Ru, Mn, Re, Cr, Mo, W, V, Nb, Ta, Ti, Zr, Hf, Rh, Pd, Ir, Pt and Os;

E is any one of H, halogen, SCN and CN;

L is any one of a phosphine ligand, a CO ligand, a pyridine ligand, a N-heterocyclic carbene ligand, a nitrile ligand and an isocyanoid ligand; and a and b are independently integers from 0-6.

4. The method according to claim 3, wherein

L is any one of trimethylphosphine, triethylphosphine, tripropylphosphine, tri-isopropylphosphine, tri-tert-butylphosphine, tricyclohexylphosphine, triphenylphosphine, methylpyridine, ethylpyridine, 1,4-bipyridine, 1,2-bis(4-pyridyl) ethylene, vinylpyridine, pyridineboronic acid, aminopyridine, cyanopyridine, pyridinethiol, ethynylpyridine, dimethylaminopyridine, ethylene pyridine, phenylpyridine, 1,2-bis(4-pyridyl) ethane, imidazole N-heterocyclic carbene, imidazoline N-heterocyclic carbene, thiazole N-heterocyclic carbene, triazole N-heterocyclic carbene, acetonitrile, propionitrile, benzonitrile, cyclohexylisocyanide, tert-butylisocyanide and phenylisocyanide;

a and b are independently integers from 0-6; when a≥2, E is different or is the same and when b≥2, L is different or is the same.

5. The method according to claim 3, the metal complex is any one of $OsCl_2(PPh_3)_3$, $RuCl_2(PPh_3)_3$, $RhCl(PPh_3)_3$ and $IrHCl_2(PPh_3)_3$.

* * * * *